(12) United States Patent
Hirokubo et al.

(10) Patent No.: US 9,347,887 B2
(45) Date of Patent: May 24, 2016

(54) WAVELENGTH VARIABLE INTERFERENCE FILTER, OPTICAL FILTER DEVICE, OPTICAL MODULE, AND ELECTRONIC APPARATUS

(71) Applicant: Seiko Epson Corporation, Tokyo (JP)

(72) Inventors: Nozomu Hirokubo, Fujimi (JP); Akira Sano, Shiojiri (JP)

(73) Assignee: Seiko Epson Corporation (JP)

( * ) Notice: Subject to any disclaimer, the term of this patent is extended or adjusted under 35 U.S.C. 154(b) by 641 days.

(21) Appl. No.: 13/626,173

(22) Filed: Sep. 25, 2012

(65) Prior Publication Data

US 2013/0083399 A1 Apr. 4, 2013

(30) Foreign Application Priority Data

Sep. 29, 2011 (JP) .................. 2011-215598

(51) Int. Cl.
*G01N 21/65* (2006.01)
*G02B 5/28* (2006.01)
*G01J 3/50* (2006.01)
*G01J 3/26* (2006.01)
*G02B 26/00* (2006.01)

(52) U.S. Cl.
CPC ............ *G01N 21/658* (2013.01); *G01J 3/26* (2013.01); *G01J 3/502* (2013.01); *G02B 5/284* (2013.01); *G02B 26/001* (2013.01)

(58) Field of Classification Search
CPC ........ G02B 5/284; G02B 5/285; G02B 5/288; G02B 6/29358; G02B 26/001; G02J 3/26
See application file for complete search history.

(56) References Cited

U.S. PATENT DOCUMENTS

| | | | |
|---|---|---|---|
| 6,888,656 B2 | 5/2005 | Miyajima et al. | |
| 7,744,220 B2 | 6/2010 | Masunishi et al. | |
| 8,149,489 B2 | 4/2012 | Shimokawa et al. | |
| 2004/0027671 A1* | 2/2004 | Wu et al. .................. | 359/578 |
| 2007/0201784 A1* | 8/2007 | Kissa et al. ................ | 385/8 |

(Continued)

FOREIGN PATENT DOCUMENTS

| | | |
|---|---|---|
| JP | 02-012218 | 1/1990 |
| JP | 2002-214561 | 7/2002 |

(Continued)

OTHER PUBLICATIONS

"Contact, n.". OED Online. Sep. 2015. Oxford University Press. http://www.oed.com/view/Entry/40021?rskey=TQPoop&result=1 &isAdvanced=false (accessed Oct. 19, 2015).*

*Primary Examiner* — Kimberly N Kakalec

(74) *Attorney, Agent, or Firm* — Harness, Dickey & Pierce, P.L.C.

(57) ABSTRACT

A wavelength variable interference filter includes a fixed substrate, a movable substrate, a fixed reflective film provided on the fixed substrate, a movable reflection film provided on the movable substrate and opposed to the fixed reflective film via an inter-reflective film gap, a fixed electrode provided on the fixed substrate, a movable electrode provided on the movable substrate and opposed to the fixed electrode via an inter-electrode gap, a fixed charging preventing electrode provided along the outer circumferential edge of the fixed electrode and in non-contact with the fixed electrode and grounded, and a movable charging preventing electrode provided along the outer circumferential edge of the movable electrode and in non-contact with the movable electrode and grounded.

12 Claims, 20 Drawing Sheets

(56) References Cited

U.S. PATENT DOCUMENTS

| | | |
|---|---|---|
| 2010/0302660 A1 | 12/2010 | Hirokubo et al. |
| 2011/0222157 A1* | 9/2011 | Sano .............................. 359/578 |
| 2011/0222158 A1* | 9/2011 | Sano .............................. 359/584 |
| 2011/0228397 A1* | 9/2011 | Matsushita ................... 359/578 |
| 2012/0162735 A1 | 6/2012 | Uchiyama et al. |
| 2012/0162736 A1 | 6/2012 | Uchiyama et al. |
| 2012/0162737 A1 | 6/2012 | Uchiyama et al. |

FOREIGN PATENT DOCUMENTS

| | | |
|---|---|---|
| JP | 2002-277758 | 9/2002 |
| JP | 2009-042458 | 2/2009 |
| JP | 2011-008225 | 1/2011 |
| JP | 2012-168362 | 9/2012 |
| WO | 2006-073111 | 7/2006 |
| WO | 2010-136654 | 12/2010 |

* cited by examiner

WAVELENGTH VARIABLE INTERFERENCE FILTER, OPTICAL FILTER DEVICE, OPTICAL MODULE, AND ELECTRONIC APPARATUS

BACKGROUND

1. Technical Field

The present invention relates to a wavelength variable interference filter, an optical filter device, an optical module, and an electronic apparatus.

2. Related Art

In the past, there is known a wavelength variable interference filter in which reflective films are respectively arranged to be opposed to each other via a predetermined gap on surfaces opposed to each other of a pair of substrates (see, for example, JP-A-2002-277758 (Patent Literature 1)).

In the wavelength variable interference filter disclosed in Patent Literature 1, reflective layers (reflective films) are respectively provided on surfaces opposed to each other of two optical substrates. Plural actuators are arranged between the optical substrates to make it possible to change the distance between the optical substrates. Further, in the wavelength variable interference filter, capacitive electrodes are respectively provided on the surfaces opposed to each other of the two optical substrates to make it possible to grasp a space between the substrates on the basis of charges stored in the capacitive electrodes.

The wavelength variable interference filter disclosed in Patent Literature 1 can measure the space between the substrates by measuring the charges stored in the capacitive electrodes. In this case, it is necessary to apply a feeble voltage between the capacitive electrodes and cause the capacitive electrodes to store the charges. However, since the charges stored in the capacitive electrodes escape to the surfaces of the substrates and the reflective films, the surfaces opposed to each other of the substrates are sometimes charged.

In general, three reasons explained below are conceivable as a reason why the charges of the capacitive electrodes escape to the surfaces of the substrates and the reflective films. First, when the surfaces of the substrates are made of a material that is easily charged, electrostatic induction is caused by an electric field generated from ends of the capacitive electrodes. The surfaces of the substrates are charged by the electrostatic induction. Second, when insulation properties of the surfaces of the substrates are low, a leak current flows on the surfaces of the substrates from the capacitive electrodes to charge the surfaces of the substrates. Further, it is conceivable that the leak current flows to the reflective films to charge the reflective films. Third, when the reflective films and the capacitive electrodes are close to each other, since capacitive coupling occurs between the capacitive electrodes and the reflective films, the reflective films are charged through the capacitive coupling.

When the substrates opposed to each other are charged in this way, a Coulomb force acts between the substrates. Therefore, it is difficult to control the distance between the reflective films.

SUMMARY

An advantage of some aspects of the invention is to provide a wavelength variable interference filter, an optical filter device, an optical module, and an electronic apparatus that prevent or reduce charging of substrates.

An aspect of the invention is directed to a wavelength variable interference filter including: a first substrate; a second substrate opposed to the first substrate; a first reflective film provided on the first substrate; a second reflective film provided on the second substrate and opposed to the first reflective film via an inter-reflective film gap; a first electrode provided on the first substrate; a second electrode provided on the second substrate and opposed to the first electrode via an inter-electrode gap; a third electrode provided along the outer circumferential edge of the first electrode and in non-contact with the first electrode and grounded; and a fourth electrode provided along the outer circumferential edge of the second electrode and in non-contact with the second electrode and grounded.

In the aspect of the invention, it is possible to adjust a space between the substrates using electrostatic attraction by applying a voltage between the first electrode and the second electrode. It is conceivable that, when the voltage is applied to the first electrode and the second electrode, charges are stored in the electrodes and the charges move onto the substrates.

To solve this problem, in the aspect of the invention, the third electrode and the fourth electrode, which are respectively in non-contact with the first electrode and the second electrode, are respectively provided along the outer circumferential edges of the first electrode and the second electrode on the first substrate and the second substrate.

With such a configuration, even if the charges stored in the first electrode move onto the first substrate on which the first electrode is provided, it is possible to allow the moved charges to escape using the third electrode. Consequently, it is possible to prevent charging of the first substrate. In other words, even if the first substrate is made of a material that is easily charged or even if electrostatic induction is caused by an electric field generated from an end of the first electrode, it is possible to suppress charging of the first substrate because the charges escape from the grounded third electrode. Even if insulation properties of the surfaces of the substrates are low and a leak current is generated, it is possible to allow the leak current to escape from the third electrode and suppress charging of the first substrate. Further, even if the positions of the first electrode and the first reflective film are close, since the grounded third electrode is provided along the outer circumferential edge of the first electrode, the grounded third electrode is interposed between the first electrode and the first reflective film. Therefore, capacitive coupling of the first electrode and the first reflective film does not occur. It is possible to suppress an inconvenience that the first reflective film is charged through the capacitive coupling.

The same applies to the second substrate. Since charges moved onto the second substrate from the second electrode can be removed by the fourth electrode, it is possible to prevent charging of the second substrate.

Consequently, since charging of the first substrate and the second substrate is prevented, it is possible to prevent generation of a Coulomb force acting between the substrates. Therefore, when a voltage is applied between the first electrode and the second electrode to adjust the inter-reflective film gap, it is possible to easily and accurately carry out the gap adjustment without being affected by the Coulomb force.

In the wavelength variable interference filter according to the aspect of the invention, it is preferable that the second substrate includes a movable section and a holding section that has a thickness dimension smaller than the thickness dimension of the movable section and holds the movable section to be capable of advancing and retracting with respect to the first substrate. The second reflective film and the second electrode are provided on the movable section.

When the second substrate is bent to the first substrate, if the entire substrate is bent, even the second reflective film bends. Therefore, it is difficult to maintain a parallel relation between the first reflective film and the second reflective film.

To solve this problem, in the configuration described above, the movable section that has the large thickness dimension and the holding section that has the thickness dimension smaller than the thickness dimension of the movable section and holds the movable section are provided on the second substrate. The second reflective film and the second electrode are provided on the movable section.

With such a configuration, the holding section is bent to advance and retract the movable section with respect to the first substrate and change the inter-reflective film gap. At this point, since the thickness dimension of the movable section is formed larger than the thickness dimension of the holding section, a bending amount of the movable section is small compared with a bending amount of the holding section. Therefore, it is possible to suppress bending of the second reflective film by providing the second reflective film in the movable section.

When the second electrode is provided on the holding section that has the small thickness dimension and tends to be bent, a bend is sometimes caused in the holding section by a film stress of the second electrode. When the holding section is bent by the film stress, it is likely that the movable section inclines, the parallel relation between the first reflective film and the second reflective film cannot be maintained, and resolution falls. In an initial state in which a voltage is not applied between the first electrode and the second electrode, when the holding section bends to the first substrate side, an initial dimension of the inter-reflective film gap decreases and a measurable wavelength region is narrowed.

To solve this problem, the second electrode is provided on the movable section. Consequently, it is possible to suppress the bending of the holding section and prevent the fall in the resolution and the narrowing of the measurable wavelength region.

In the wavelength variable interference filter according to the aspect of the invention, it is preferable that the fourth electrode is provided on the movable section.

In this configuration, the fourth electrode is provided on the movable section. Consequently, it is possible to reduce the influence on the second substrate due to the film stress of the fourth electrode and prevent the bending of the second substrate.

In the wavelength variable interference filter according to the aspect of the invention, it is preferable that the fourth electrode is provided over the entire surface of the holding section opposed to the first substrate.

In this configuration, the fourth electrode is provided to cover the entire holding section. The holding section is a portion that bends when the movable section is displaced and is a portion that is most easily bent by the influence of a Coulomb force or the like. Since the fourth electrode is provided to cover the holding section, it is possible to more surely prevent charging in the holding section and more surely prevent bending of the holding section due to the Coulomb force.

In the wavelength variable interference filter according to the aspect of the invention, it is preferable that the fourth electrode includes a plurality of openings, from which the holding section is exposed, in plan view of the second substrate viewed from the substrate thickness direction. The openings are equally arranged over the entire surface of the holding section opposed to the first substrate.

Examples of a configuration in which "the openings are equally arranged over the entire surface of the holding section opposed to the first substrate" include a configuration in which plural ring-shaped electrodes having a center point same as the center point of the movable section are arranged at equal intervals and openings are formed among the electrodes and a mesh configuration in which plural openings are provided by a mesh-like electrode.

In the configuration described above, the fourth electrode having the plural openings is provided on the holding section that is easily affected by a film stress. Therefore, for example, compared with the fourth electrode that covers the entire surface of the holding section oppose to the first substrate, it is possible to reduce the influence of the film stress on the holding section and suppress bending of the holding section due to the film stress.

In the wavelength variable interference filter according to the aspect of the invention, it is preferable that the third electrode is connected to the first reflective film. The fourth electrode is connected to the second reflective film. With such a configuration, the first reflective film is connected to the third electrode and the second reflective film is connected to the fourth electrode. Therefore, it is possible to more surely prevent charging of the first reflective film and the second reflective film. Both the first reflective film and the second reflective film are grounded and set to the same potential (zero potential). Therefore, it is possible to surely prevent the influence of a Coulomb force between the reflective films.

Further, the third electrode and the fourth electrode are grounded and the first reflective film and the second reflective film are set to zero potential. Therefore, it is possible to suppress adhesion of floating charges (charged substances) in the air.

In the wavelength variable interference filter according to the aspect of the invention, it is preferable that the wavelength variable interference filter includes a first detection electrode connected to the first reflective film and a second detection electrode connected to the second reflective film. The third electrode is provided along the outer circumferential edge of the first detection electrode and in non-contact with the first detection electrode. The fourth electrode is provided along the outer circumferential edge of the second detection electrode and in non-contact with the second detection electrode.

As the first detection electrode and the second detection electrode, for example, a capacitance detection electrode for measuring the inter-reflective film gap can be illustrated. When such a capacitance detection electrode is used, it is possible to measure the inter-reflective film gap by applying a feeble voltage between the first detection electrode and the second detection electrode, causing the first reflective film and the second reflective film to store charges, and detecting charge storage amounts of the reflective films at the time when the inter-reflective film gap is changed.

In the configuration described above, the third electrode is provided along the outer circumferential edge of the first detection electrode. The fourth electrode is provided along the outer circumferential edge of the second detection electrode. Therefore, it is possible to prevent movement of charges from the first detection electrode and the second detection electrode to the first substrate and the second substrate. It is possible to prevent generation of a Coulomb force due to charging of the first substrate and the second substrate.

In the wavelength variable interference filter according to the aspect of the invention, it is preferable that the dimension of the inter-reflective film gap is changed by applying a voltage between the first electrode and the second electrode. According to this configuration, it is possible to easily change the dimension of the inter-reflective film gap using electrostatic attraction by applying a voltage between the first electrode and the second electrode. The first electrode and the second electrode are charged by the voltage application. However, as explained above, even if charges of the first electrode and the second electrode move onto the substrates, it is possible to allow the charges to escape from the third electrode and the fourth electrode.

Another aspect of the invention is directed to a wavelength variable interference filter including: a substrate; a reflecting section provided on the substrate; an electrode provided on the substrate; and a grounded electrode provided along the outer circumferential edge of the electrode and in non-contact with the electrode and grounded.

According to this aspect of the invention, as in the aspect of the invention explained above, it is possible to allow charges moved onto the substrate from the electrode to escape from the grounded electrode. Therefore, it is possible to prevent charging of the substrate.

Still another aspect of the invention is directed to a wavelength variable interference filter including: a first substrate; a second substrate opposed to the first substrate; a first reflective film provided on the first substrate; a second reflective film provided on the second substrate and opposed to the first reflective film via an inter-reflective film gap; a first electrode provided on the first substrate; a second electrode provided on the second substrate and opposed to the first electrode via an inter-electrode gap; a third electrode provided along the outer circumferential edge of the first electrode and in non-contact with the first electrode and fixed to reference potential; and a fourth electrode provided along the outer circumferential edge of the second electrode and in non-contact with the second electrode and fixed to the reference potential.

In this aspect of the invention, the third electrode and the fourth electrode are fixed to the reference potential. With such a configuration, as in the configuration explained above, it is possible to allow charges moved onto the substrates from the first electrode and the second electrode to escape from the third electrode and the fourth electrode. Since the third electrode and the fourth electrode have the same potential, a Coulomb force such as electrostatic attraction does not act between the third electrode and the fourth electrode. It is possible to carry out accurate setting of the inter-reflective film gap using the first electrode and the second electrode. Yet another aspect of the invention is directed to an optical filter device including: a wavelength variable interference filter including: a first substrate; a second substrate opposed to the first substrate; a first reflective film provided on the first substrate; a second reflective film provided on the second substrate and opposed to the first reflective film via an inter-reflective film gap; a first electrode provided on the first substrate; a second electrode provided on the second substrate and opposed to the first electrode via an inter-electrode gap; a third electrode provided along the outer circumferential edge of the first electrode and in non-contact with the first electrode and grounded; and a fourth electrode provided along the outer circumferential edge of the second electrode and in non-contact with the second electrode and grounded; and a housing that stores the wavelength variable interference filter.

In this aspect of the invention, as in the aspects of the invention explained above, it is possible to allow charges moved from the first electrode and the second electrode to escape using the grounded third and fourth electrodes. It is possible to prevent the influence of a Coulomb force. Therefore, it is possible to easily and accurately carry out adjustment of the inter-reflective film gap using the first electrode and the second electrode.

Since the wavelength variable interference filter is stored in the housing, an impact from the outside is less easily transmitted to the wavelength variable interference filter. It is possible to prevent breakage of the wavelength variable interference filter.

Still yet another aspect of the invention is directed to an optical module including: a first substrate; a second substrate opposed to the first substrate; a first reflective film provided on the first substrate; a second reflective film provided on the second substrate and opposed to the first reflective film via an inter-reflective film gap; a first electrode provided on the first substrate; a second electrode provided on the second substrate and opposed to the first electrode via an inter-electrode gap; a third electrode provided along the outer circumferential edge of the first electrode and in non-contact with the first electrode and grounded; a fourth electrode provided along the outer circumferential edge of the second electrode and in non-contact with the second electrode and grounded; and a detecting section that detects light extracted by the first reflective film and the second reflective film.

In this aspect of the invention, as in the aspects of the invention explained above, it is possible to allow charges moved from the first electrode and the second electrode to escape using the grounded third and fourth electrodes. It is possible to prevent the influence of a Coulomb force. Therefore, it is possible to easily and accurately carry out adjustment of the inter-reflective film gap using the first electrode and the second electrode.

Since the Coulomb force does not act between the first substrate and the second substrate and between the first reflective film and the second reflective film, it is possible to accurately adjust the inter-reflective film gap. It is possible to extract light having desired target wavelength from the wavelength variable interference filter. Therefore, it is possible to accurately detect an accurate amount of the light having the target wavelength by detecting an amount of the like in the detecting section.

Further another aspect of the invention is directed to an electronic apparatus including: a first substrate; a second substrate opposed to the first substrate; a first reflective film provided on the first substrate; a second reflective film provided on the second substrate and opposed to the first reflective film via an inter-reflective film gap; a first electrode provided on the first substrate; a second electrode provided on the second substrate and opposed to the first electrode via an inter-electrode gap; a third electrode provided along the outer circumferential edge of the first electrode and in non-contact with the first electrode and grounded; and a fourth electrode provided along the outer circumferential edge of the second electrode and in non-contact with the second electrode and grounded.

In this aspect of the invention, as in the aspects of the invention explained above, it is possible to allow charges moved from the first electrode and the second electrode to escape using the grounded third and fourth electrodes. It is possible to prevent the influence of a Coulomb force. Therefore, it is possible to easily and accurately carry out adjustment of the inter-reflective film gap using the first electrode and the second electrode.

Therefore, in the electronic apparatus, for example, when light having a target wavelength extracted because of light interference by the first reflective film and the second reflective film is detected and various kinds of processing are carried out on the basis of an amount of the light, it is possible to accurately detect an amount of the light having the target wavelength. Therefore, it is possible to improve processing accuracy of the various kinds of processing.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

A first embodiment of the invention is explained below with reference to the accompanying drawings.

1. Schematic Configuration of a Colorimetric Apparatus

Figure 1:
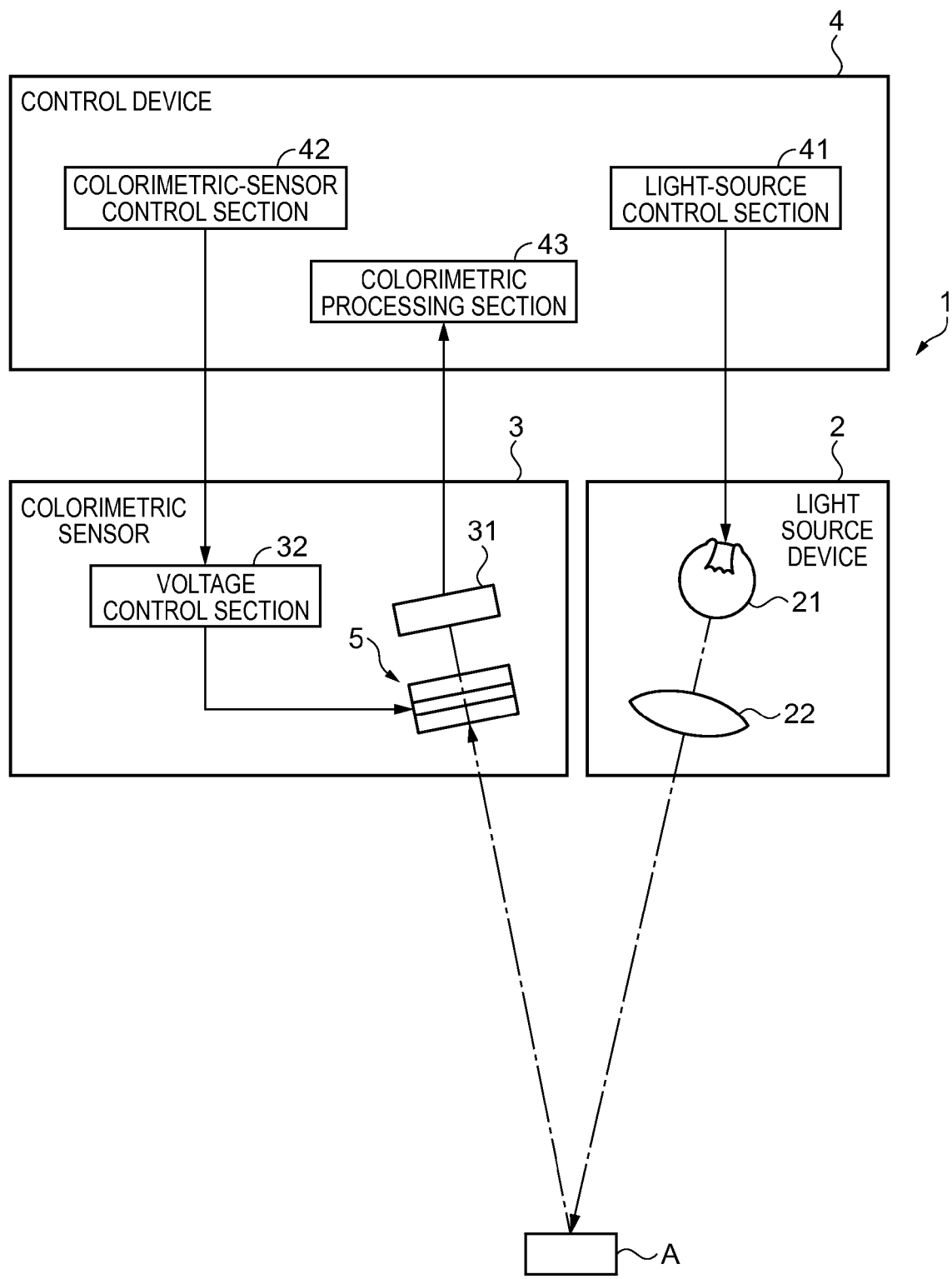
FIG. 1 is a block diagram showing a schematic configuration of a colorimetric apparatus according to a first embodiment of the invention.

FIG. 1 is a block diagram of a schematic configuration of a colorimetric apparatus 1 (an electronic apparatus) according to this embodiment.

The colorimetric apparatus 1 includes, as shown in FIG. 1, a light source device 2 that emits light to an inspection target A, a colorimetric sensor 3 (an optical module), and a control device 4 that controls an overall operation of the colorimetric apparatus 1. The calorimetric apparatus 1 is an apparatus that reflects the light emitted from the light source device 2 on the inspection target A, receives reflected inspection target light in the colorimetric sensor 3, and analyzes and measures the chromaticity of the inspection target light, i.e., a color of the inspection target A on the basis of a detection signal output from the colorimetric sensor 3.

2. Configuration of the Light Source Device

The light source device 2 includes alight source 21 and plural lenses 22 (only one is shown in FIG. 1). The light source device 2 emits white light to the inspection target A. The plural lenses 22 may include a collimator lens. In this case, the light source device 2 converts the white light emitted from the light source 21 into parallel light using the collimator lens and emits the parallel light to the inspection target A from a not-shown projection lens. In this embodiment, the colorimetric apparatus 1 including the light source device 2 is illustrated. However, for example, when the inspection target A is a light emitting member such as a liquid crystal panel, the light source device 2 does not have to be provided.

3. Configuration of the Colorimetric Sensor

The colorimetric sensor 3 includes, as shown in FIG. 1, a wavelength variable interference filter 5, a detecting section 31 that receives light transmitted through the wavelength variable interference filter 5, and a voltage control section 32 that changes the wavelength of the light transmitted through the wavelength variable interference filter 5. The colorimetric sensor 3 includes, in a position opposed to the wavelength variable interference filter 5, a not-shown incident optical lens that guides the reflected light (the inspection target light) reflected by the inspection target A to the inside. The colorimetric sensor 3 splits, with the wavelength variable interference filter 5, light having predetermined wavelength in the inspection target light made incident from the incident optical lens and receives the split light in the detecting section 31.

The detecting section 31 includes plural photoelectric conversion elements. The detecting section 31 generates an electric signal corresponding to a received light amount. The detecting section 31 is connected to the control device 4. The detecting section 31 outputs the generated electric signal to the control device 4 as a light reception signal.

3-1. Configuration of the Wavelength Variable Interference Filter

Figure 2:
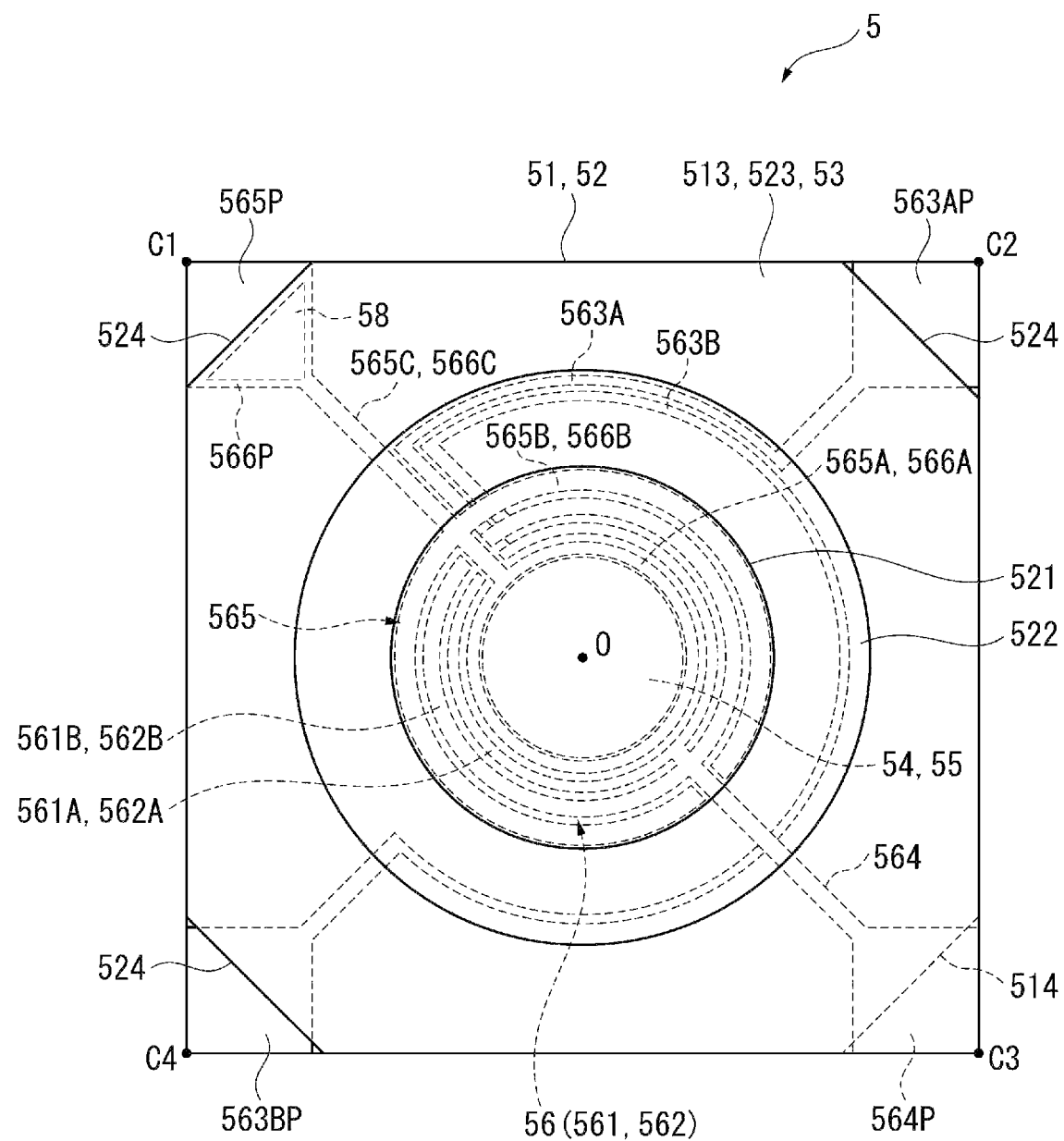
FIG. 2 is a plan view showing a schematic configuration of a wavelength variable interference filter according to the first embodiment.
Figure 3:
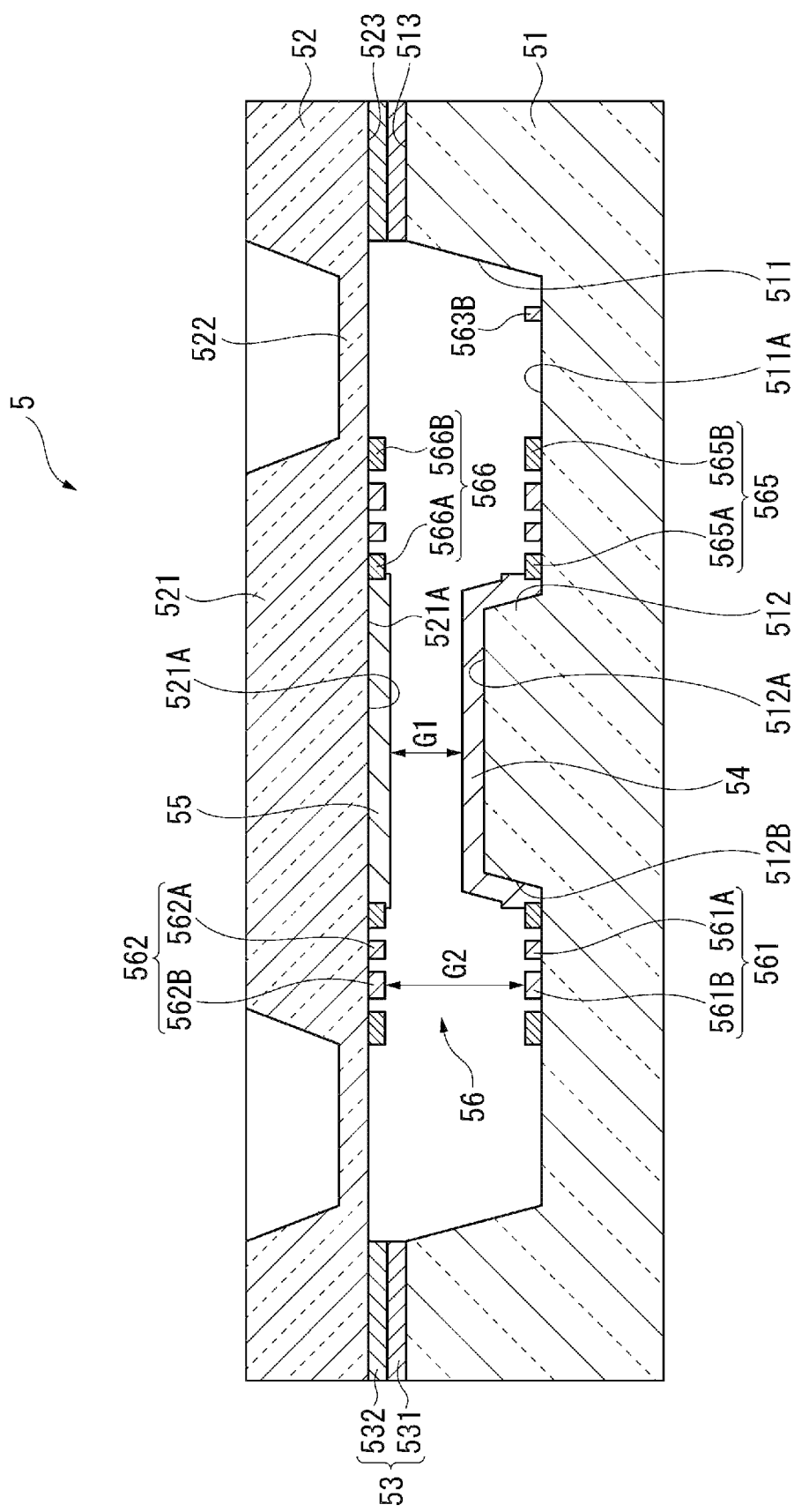
FIG. 3 is a sectional view showing a schematic configuration of the wavelength variable interference filter according to the first embodiment.

FIG. 2 is a plan view showing a schematic configuration of the wavelength variable interference filter 5. FIG. 3 is a sectional view showing a schematic configuration of the wavelength variable interference filter 5.

As shown in FIG. 2, the wavelength variable interference filter 5 is a tabular optical member having, for example, a plane square shape. The wavelength variable interference filter 5 includes, as shown in FIG. 3, a fixed substrate 51, which is the first substrate in the embodiment of the invention, and a movable substrate 52, which is the second substrate in the embodiment of the invention. Each of the fixed substrate 51 and the movable substrate 52 is formed of any one of various glasses such as soda glass, crystalline glass, quartz glass, lead glass, potassium glass, borosilicate glass, and no-alkali glass, quartz, and the like. A first bonding section 513 and a second bonding section 523 formed near the outer circumferential portions of the fixed substrate 51 and the movable substrate 52 are bonded to a bonding film 53 formed of plasma polymer films 531 and 532 containing, for example, siloxane, whereby the fixed substrate 51 and the movable substrate 52 are integrally formed.

A fixed reflective film 54, which forms the first reflective film and the reflecting section in the embodiment of the invention, is provided on the fixed substrate 51. A movable reflective film 55, which forms the second reflective film and the reflecting section in the embodiment of the invention, is provided on the movable substrate 52. The fixed reflective film 54 and the movable reflective film 55 are arranged to be opposed to each other via an inter-reflective film gap G1. In the wavelength variable interference filter 5, an electrostatic actuator 56 used for adjusting the dimension of the inter-reflective film gap G1 between the fixed reflective film 54 and the movable reflective film 55 is provided. The electrostatic actuator 56 includes a fixed electrode 561, which forms the first electrode and the electrode in the embodiment of the invention, provided on the fixed substrate 51 and a movable electrode 562, which forms the second electrode and the electrode in the embodiment of the invention, provided on the movable substrate 52. The electrodes 561 and 562 may be respectively directly provided on the substrate surfaces of the fixed substrate 51 and the movable substrate 52 or may be provided via other film members.

In plan view shown in FIG. 2 of the wavelength variable interference filter 5 viewed from the substrate thickness direction of the fixed substrate 51 (the movable substrate 52), a plane center point O of the fixed substrate 51 and the movable substrate 52 coincides with a center point of the fixed reflective film 54 and the movable reflective film 55 and coincides with a center point of a movable section 521 explained below. In the following explanation, plan view of the wavelength variable interference filter 5 viewed from the substrate thickness direction of the fixed substrate 51 or the movable substrate 52, i.e., plan view of the wavelength variable interference filter 5 viewed from the laminating direction of the fixed substrate 51, the bonding film 53, and the movable substrate 52 is referred to as filter plan view.

3-1-1. Configuration of the Fixed Substrate

Figure 4:
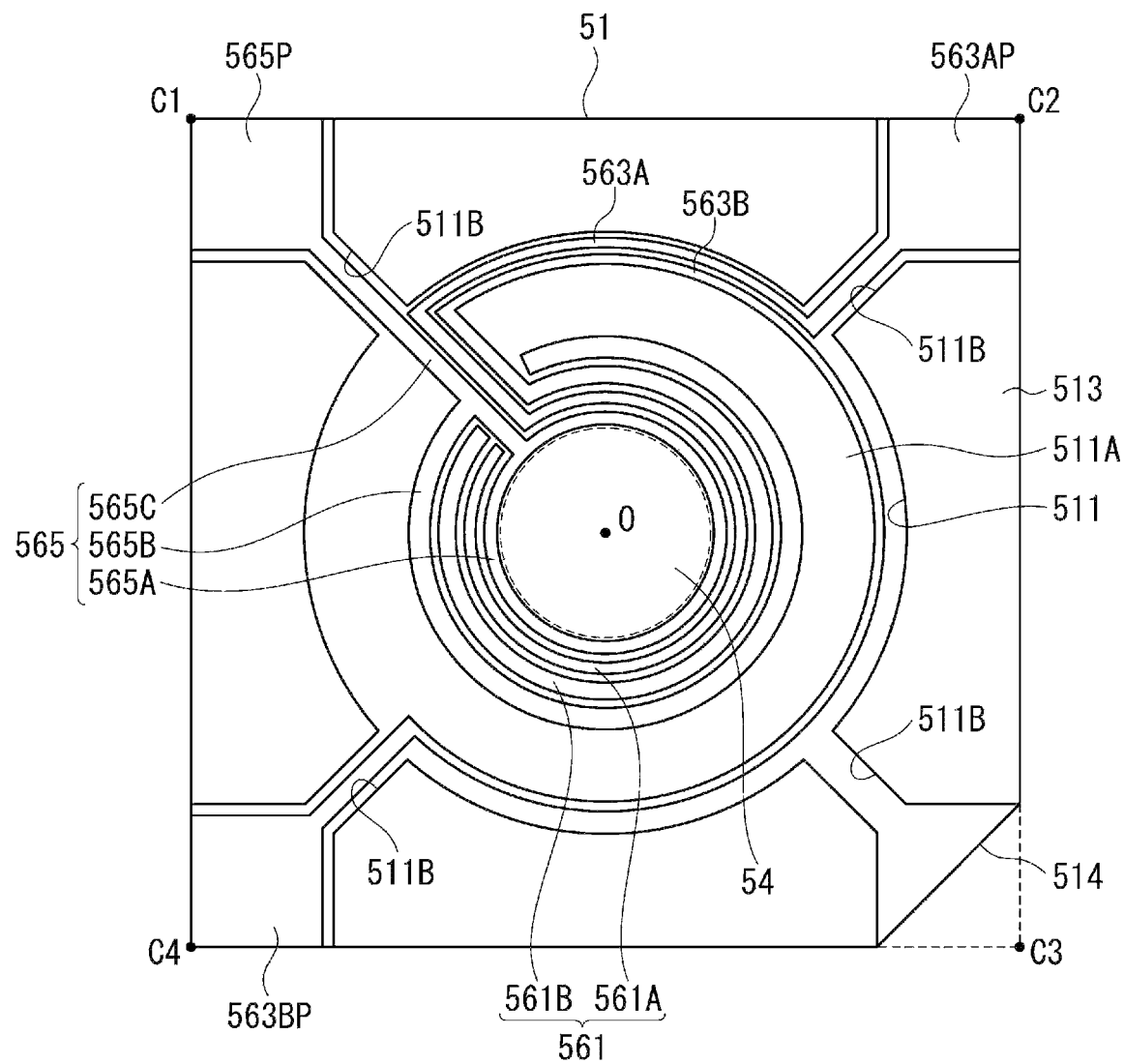
FIG. 4 is a plan view of a fixed substrate viewed from a movable substrate side in the first embodiment.

FIG. 4 is a plan view of the fixed substrate 51 in this embodiment viewed from the movable substrate 52 side.

The fixed substrate 51 is formed by machining a glass base material formed in thickness of, for example, 1 mm. Specifically, as shown in FIG. 3, an electrode arranging groove 511 and a reflective-film setting section 512 (see FIG. 3) are formed on the fixed substrate 51 by etching. The fixed substrate 51 is formed in a thickness dimension larger than the thickness dimension of the movable substrate 52. A bend of the fixed substrate 51 due to electrostatic attraction caused when a voltage is applied between the fixed electrode 561 and the movable electrode 562 or internal stress of the fixed electrode 561 does not occur.

A cutout section 514 is formed at a vertex C3 (see FIGS. 2 and 4) of the fixed substrate 51. A movable electrode pad 564P explained below is exposed on the fixed substrate 51 side of the wavelength variable interference filter 5. The electrode arranging groove 511 is formed in an annular shape having the center at the plane center point O of the fixed substrate 51 in the filter plan view. The reflective-film setting section 512 is formed to project to the movable substrate 52 side from the center of the electrode arranging groove 511 in the plan view. The groove bottom surface of the electrode arranging groove 511 is an electrode setting surface 511A on which the fixed electrode 561 is arranged. A projecting distal end face of the reflective-film setting section 512 is a reflective-film setting surface 512A.

Electrode extracting grooves 511B extending from the electrode arranging groove 511 to vertexes C1, C2, C3, and C4 at the outer circumferential edge of the fixed substrate 51 are provided on the fixed substrate 51.

A fixed electrode 561 is formed on the electrode setting surface 511A. The fixed electrode 561 includes a fixed inner electrode 561A provided on the reflective-film setting section 512 side in the electrode setting surface 511A and a fixed outer electrode 561B provided further on the outer circumferential side than the fixed inner electrode 561A while not being in contact with the fixed inner electrode 561A.

Each of the fixed inner electrode 561A and the fixed outer electrode 561B is formed in a substantially C shape. An opened portion of the letter C is provided in a part near, for example, the vertex C1.

In the fixed substrate 51, a fixed inner extracting electrode 563A and a fixed outer extracting electrode 563B extending from ends of the opened portions of the letter C of the fixed inner electrode 561A and the fixed outer electrode 561B are provided.

As shown in FIG. 4, the fixed inner extracting electrode 563A extends from the end of the opened portion of the letter C of the fixed inner electrode 561A to the diameter outer side, extends from the end of the extension to the electrode extracting groove 511B corresponding to the vertex C2 along the outer circumferential edge of the electrode setting surface 511A, and further extends from the end of the extension to the vertex C2 along the electrode extracting groove 511B. An extension distal end (a portion located at the vertex C2 of the fixed substrate 51) of the fixed inner extracting electrode 563A forms a fixed inner electrode pad 563AP connected to the voltage control section 32.

As shown in FIG. 4, the fixed outer extracting electrode 563B extends from the end of the opened portion of the letter C of the fixed outer electrode 561B to the diameter outer side, extends from the end of the extension to the electrode extracting groove 511B corresponding to the vertex C4 along the outer circumferential edge of the electrode setting surface 511A, and further extends from the end of the extension to the vertex C4 along the electrode extracting groove 511B. An extension distal end (a portion located at the vertex C4 of the fixed substrate 51) of the fixed outer extracting electrode 563B forms a fixed outer electrode pad 563BP connected to the voltage control section 32.

As the fixed electrode 561, the fixed inner extracting electrode 563A, and the fixed outer extracting electrode 563B, any electrode material may be used as long as the electrode material is a conductive film. For example, an ITO, a Cr/Au laminated electrode, or the like can be used.

On the fixed electrode 561, an insulative film may be laminated in order to secure a dielectric voltage between the fixed electrode 561 and the movable electrode 562.

On the fixed substrate 51, a fixed charging preventing electrode 565, which forms a first charging preventing electrode functioning as the third electrode and the grounded electrode in the embodiment of the invention, is further provided. The fixed charging preventing electrode 565 is formed in non-contact with the fixed electrode 561 along the outer circumferential edge of the fixed electrode 561. Specifically, the fixed charging preventing electrode 565 includes an annular fixed inner charging preventing electrode 565A provided on the inner diameter side (the reflective-film setting section 512 side) of the fixed inner electrode 561A, a C-shaped fixed outer charging preventing electrode 565B provided on the outer diameter side of the fixed outer electrode 561B, and a fixed charging preventing extracting electrode 565C that passes the opened portion of the letter C of the fixed electrode 561.

In the fixed inner charging preventing electrode 565A, the fixed reflective film 54 is laminated in the annular inner circumferential portion.

The fixed charging preventing extracting electrode 565C connects the fixed inner charging preventing electrode 565A and the fixed outer charging preventing electrode 565B and extends in the diameter outer direction away from the plane center point O. The fixed charging preventing extracting electrode 565C is extended from the electrode extracting groove 511B corresponding to the vertex C1 to the vertex C1 of the fixed substrate 51. An extension distal end (a portion located at the vertex C2 of the fixed substrate 51) of the fixed charging preventing extracting electrode 565C forms a fixed charging preventing electrode pad 565P connected to the voltage control section 32. The voltage control section 32 connects the fixed charging preventing electrode pad 565P to a GND circuit. Consequently, the fixed charging preventing electrode 565 is grounded and maintained at zero potential.

As explained above, the reflective-film setting section 512 is formed coaxially with the electrode arranging groove 511 and in a substantially columnar shape having a diameter dimension smaller than the diameter dimension of the electrode arranging groove 511. The reflective-film setting section 512 includes the reflective-film setting surface 512A opposed to the movable substrate 52 of the reflective-film setting section 512 and a side section 512B that forms the outer circumferential surface of the reflective-film setting section 512. The electrode arranging groove 511 and the reflective-film setting section 512 are formed by etching the fixed substrate 51. Therefore, as shown in FIG. 3, the side section 512B is a curved surface inclining with respect to the substrate thickness direction because of the influence of side etching.

As shown in FIGS. 2 to 4, the fixed reflective film 54 is provided on the reflective-film setting section 512. The fixed reflective film 54 is formed from the reflective-film setting surface 512A to a part of the inner circumferential side of the electrode extracting groove 511B. As explained above, the outer circumferential portion is laminated in the annular inner circumferential portion of the fixed inner charging preventing electrode 565A. Consequently, the fixed reflective film 54 and the fixed charging preventing electrode 565 are electrically connected.

As the fixed reflective film 54, for example, a metal film of Ag or the like or an alloy film of an Ag alloy or the like can be used. For example, a dielectric multilayer film in which a high refractive layer is formed of $TiO_2$ and a low refractive layer is formed of $SiO_2$ may be used. When the dielectric multilayer film is used as the fixed reflective film 54, it is desirable to separately laminate a metal film or an alloy film on the outermost layer surface of the fixed reflective film 54 to secure conduction with the fixed inner charging preventing electrode 565A.

Since the fixed reflective film 54 in this embodiment is connected to the fixed charging preventing electrode 565, as shown in FIG. 3, the fixed reflective film 54 is formed to cover the entire reflective-film setting section 512. Since the side section 512B inclines with respect to the substrate thickness direction, for example, when a reflective film is formed by vapor deposition or the like, the reflective film is formed on the side section 512B as well. Therefore, light extracted by the fixed reflective film 54 and the movable reflective film 55 arranged on an optical path that passes the side section 512B has wavelength different from the wavelength of light extracted by the fixed reflective film 54 and the movable reflective film 55 arranged on an optical path that passes the reflective-film setting surface 512A. Therefore, in order to prevent light that passes the side section 512B from being detected by the detecting section 31, it is desirable to provide a not-shown aperture for defining a light interference region of the fixed reflective film 54 and the movable reflective film 55. As the aperture, for example, when the fixed charging preventing electrode 565 is formed by a non-translucent conductive film, the annular inner circumferential edge of the fixed inner charging preventing electrode 565A may be used. In this case, the fixed charging preventing electrode 565 only has to be formed such that the inner circumferential edge of the fixed inner charging preventing electrode 565A is present within the reflective-film setting surface 512A. Besides, as the aperture, the inner circumferential edge of a movable inner charging preventing electrode 566A provided on the movable substrate 52 may be used. The aperture may be formed by providing a light blocking section on the outer side surface (a surface on which the fixed reflective film 54 and the movable reflective film 55 are not provided) of the fixed substrate 51 or the movable substrate 52. Further, the aperture may be provided, for example, on an optical path in the colorimetric sensor 3 on the outside of the wavelength variable interference filter 5.

On a light incident surface (a surface on which the fixed reflective film 54 is not provided) of the fixed substrate 51, a reflection preventing film may be formed in a position corresponding to the fixed reflective film 54. The reflection preventing film can be formed by alternately laminating a low refractive index film and a high refractive index film. The reflection preventing film reduces the reflectance of visible light on the surface of the fixed substrate 51 and increases the transmittance of the visible light.

3-1-2. Configuration of the Movable Substrate

Figure 5:
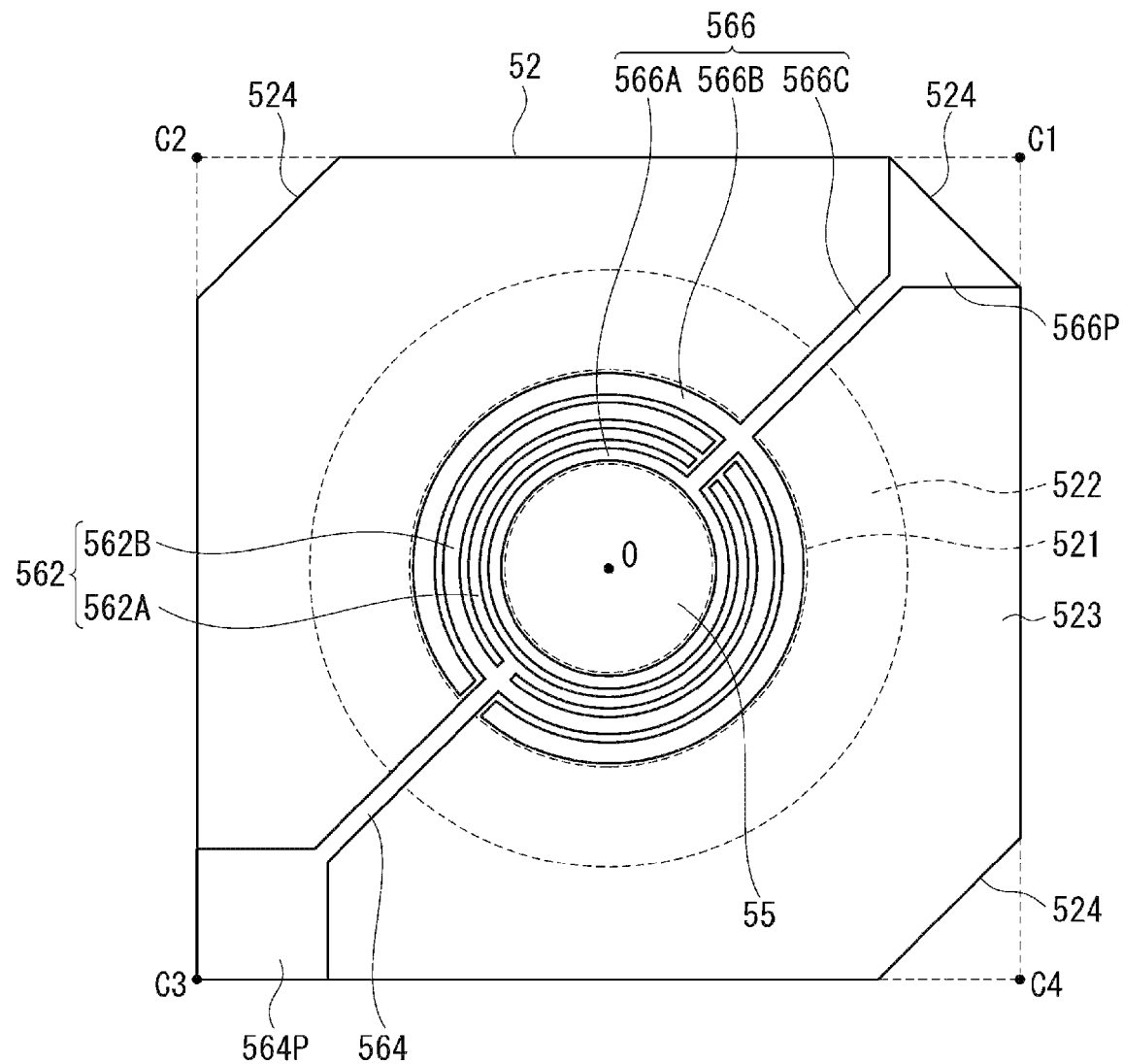
FIG. 5 is a plan view of the movable substrate viewed from the fixed substrate side in the first embodiment.

FIG. 5 is a plan view of the movable substrate viewed from the fixed substrate side in the first embodiment.

The movable substrate 52 is formed by etching a glass base material formed in thickness of, for example, 600 μm.

Specifically, the movable substrate 52 includes, in the filter plan view shown in FIGS. 2 and 5, a movable section 521 formed in a circular shape having the center in the plane center point O and a holding section 522 that is coaxial with the movable section 521 and holds the movable section 521.

In the movable substrate 52, as shown in FIGS. 2 and 5, cutout sections 524 are formed to correspond to the vertexes C1, C2, and C4. When the wavelength variable interference filter 5 is viewed from the movable substrate 52 side, the fixed inner electrode pad 563AP, the fixed outer electrode pad 563BP, and the fixed charging preventing electrode pad 565P are exposed. The movable section 521 is formed in a thickness dimension larger than the thickness dimension of the holding section 522. For example, in this embodiment, the movable section 521 is formed in a dimension same as the thickness dimension of the movable substrate 52. In the filter plan view, the movable section 521 is formed at least in a diameter dimension larger than the diameter dimension of the outer circumferential edge of the fixed outer charging preventing electrode 565B. The movable electrode 562, a movable charging preventing electrode 566, and the movable reflective film 55 are provided on the movable section 521.

As in the fixed substrate 51, a reflection preventing film may be formed on the surface of the movable section 521 on the opposite side of the fixed substrate 51. The reflection preventing film can be formed by alternately laminating a low refractive index film and a high refractive index film. It is possible to reduce the reflectance of visible light on the surface of the movable substrate 52 and increase the transmittance of the visible light.

The movable electrode 562 is opposed to the fixed electrode 561 via an inter-electrode gap G2 (G2>G1). The movable electrode 562 includes a movable inner electrode 562A having the same shape as the fixed inner electrode 561A and opposed to the fixed inner electrode 561A and a movable outer electrode 562B having the same shape as the fixed outer electrode 561B and opposed to the fixed outer electrode 561B. A state in which the fixed inner electrode 561A and the movable inner electrode 562A are opposed to each other (a state in which the fixed outer electrode 561B and the movable outer electrode 562B are opposed to each other) means that the fixed inner electrode 561A and the movable inner electrode 562A (the fixed outer electrode 561B and the movable outer electrode 562B) overlap in the filter plan view.

The movable substrate 52 includes, in the movable inner electrode 562A, a movable extracting electrode 564 that connects the fixed inner electrode 561A and the movable inner electrode 562A and extends in the diameter outer direction away from the plane center point O. The movable extracting electrode 564 extends to the vertex C3 of the movable substrate 52. An extension distal end (a portion located at the vertex C3 of the movable substrate 52) of the movable extracting electrode 564 forms a movable electrode pad 564P connected to the voltage control section 32.

On the movable substrate 52, the movable charging preventing electrode 566, which forms a second charging preventing electrode functioning as the fourth electrode and the grounded electrode in the embodiment of the invention, is provided. The movable charging preventing electrode 566 includes, in the movable surface 521A, the movable inner charging preventing electrode 566A opposed to the fixed inner charging preventing electrode 565A, a movable outer charging preventing electrode 566B opposed to the fixed outer charging preventing electrode 565B, and a movable charging preventing extracting electrode 566C opposed to the fixed charging preventing extracting electrode 565C.

In the movable inner charging preventing electrode 566A, as in the fixed inner charging preventing electrode 565A, the movable reflective film 55 is laminated to overlap the annular inner circumferential portion. The movable reflective film 55 and the movable inner charging preventing electrode 566A are electrically connected.

The movable charging preventing extracting electrode 566C connects the fixed inner charging preventing electrode 565A and the fixed outer charging preventing electrode 565B and extends in the diameter outer direction from the movable surface 521A to the vertex C1. An extension distal end (near the vertex C2 of the movable substrate 52) of the movable charging preventing extracting electrode 566C forms a movable charging preventing electrode pad 566P. The movable charging preventing electrode pad 566P is electrically connected to the fixed charging preventing electrode pad 565P by a conductive member 58 (see FIG. 2) such as Ag paste. Consequently, the fixed charging preventing electrode 565 is grounded by the GND circuit of the voltage control section 32 and maintained at zero potential.

As the movable reflective film 55, a reflective film having a configuration same as the configuration of the fixed reflective film 54 is used. As explained above, in the movable reflective film 55, the outer circumferential portion is laminated on the annular inner circumferential portion of the movable inner charging preventing electrode 566A. Consequently, the movable reflective film 55 and the movable charging preventing electrode 566 are electrically connected. When a dielectric multilayer film is used as the movable reflective film 55, it is desirable to separately laminate a metal film or an alloy film on the outermost layer surface of the movable reflective film 55 to secure conduction with the movable inner charging preventing electrode 566A.

The holding section 522 is a diaphragm that surrounds the movable section 521. The holding section 522 is formed in a thickness dimension of, for example, 30 μm and formed to have rigidity in the thickness direction smaller than the rigidity of the movable section 521.

Therefore, the holding section 522 more easily bends than the movable section 521. It is possible to bend the holding section 522 to the fixed substrate 51 side with slight electrostatic attraction. When the holding section 522 is bent, since the movable section 521 has the thickness dimension and the rigidity larger than the thickness dimension and the rigidity of the holding section 522, even if force for bending the movable substrate 52 acts with electrostatic attraction, there is almost no bend of the movable section 521. A bend of the movable reflective film 55 formed on the movable section 521 can also be prevented.

In this embodiment, the diaphragm-like holding section 522 is illustrated. However, the holding section is not limited to this. For example, beam-like holding sections arranged at equal angle intervals may be provided around the plane center point O.

3-2. Configuration of the Voltage Control Section

The voltage control section 32 is connected to the fixed inner electrode pad 563AP, the fixed outer electrode pad 563BP, the movable electrode pad 564P, and the fixed charging preventing electrode pad 565P. The voltage control section 32 applies a voltage to the electrostatic actuator 56 to drive the electrostatic actuator 56 by setting the fixed inner electrode pad 563AP, the fixed outer electrode pad 563BP, and the movable electrode pad 564P to predetermined potential on the basis of a control signal input from the control device 4. In this embodiment, different voltages are respectively applied between the fixed inner electrode 561A and the movable inner electrode 562A and between the fixed outer electrode 561B and the movable outer electrode 562B. Consequently, it is possible to cause different electrostatic attractions to respectively act on the fixed inner electrode 561A, the movable inner electrode 562A, the fixed outer electrode 561B, and the movable outer electrode 562B. It is possible to perform more accurate adjustment of the inter-reflective film gap G1. As explained above, the voltage control section 32 includes the GND circuit. The fixed charging preventing electrode pad 565P is grounded. Consequently, the fixed charging preventing electrode 565 and the movable charging preventing electrode 566 connected to the fixed charging preventing electrode pad 565P are maintained at zero potential.

In the example explained in this embodiment, the fixed charging preventing electrode 565 and the movable charging preventing electrode 566 connected to the fixed charging preventing electrode pad 565P are grounded and maintained at zero potential by the GND circuit provided in the voltage control section 32. However, for example, the fixed charging preventing electrode 565 and the movable charging preventing electrode 566 may be maintained, for example, at fixed reference potential.

In this case, as in the example explained above, it is possible to allow charges moved from the fixed electrode 561 and the movable electrode 562 to escape from the fixed charging preventing electrode 565 and the movable charging preventing electrode 566. Since the fixed charging preventing electrode 565 and the movable charging preventing electrode 566 are maintained at the same potential (the reference potential), no Coulomb force acts between the fixed charging preventing electrode 565 and the movable charging preventing electrode

566. It is possible to accurately carry out adjustment of the inter-reflective film gap G1 by the electrostatic actuator 56.

4. Configuration of the Control Device

The control device 4 controls the overall operation of the colorimetric apparatus 1.

As the control device 4, for example, a general-purpose personal computer, a portable information terminal, a computer exclusive for colorimetry, or the like can be used.

The control device 4 includes, as shown in FIG. 1, a light-source control section 41, a colorimetric-sensor control section 42, and a colorimetric processing section 43, which forms an analysis processing section in the embodiment of the invention.

The light-source control section 41 is connected to the light source device 2. The light-source control section 41 outputs a predetermined control signal to the light source device 2 on the basis of, for example, a setting input of a user and causes the light source device 2 to emit white light having predetermined brightness.

The colorimetric-sensor control section 42 is connected to the colorimetric sensor 3. The colorimetric-sensor control section 42 sets the wavelength of light received by the colorimetric sensor 3 on the basis of, for example, a setting input of the user and outputs a control signal for instructing to detect a received light amount of the light having the wavelength to the colorimetric sensor 3. The voltage control section 32 of the colorimetric sensor 3 sets, on the basis of the control signal, an applied voltage to the electrostatic actuator 56 to transmit only wavelength of light desired by the user.

The colorimetric processing section 43 analyzes the chromaticity of the inspection target A from the received light amount detected by the detecting section 31.

5. Manufacturing Method for the Wavelength Variable Interference Filter

A manufacturing method for the wavelength variable interference filter 5 is explained with reference to FIGS. 6A to 6F and FIGS. 7A to 7E.

In order to manufacture the wavelength variable interference filter 5, the fixed substrate 51 and the movable substrate 52 are separately manufactured and the manufactured fixed substrate 51 and the manufactured movable substrate 52 are stuck together.

5-1. Fixed Substrate Manufacturing Process

Figure 6A:
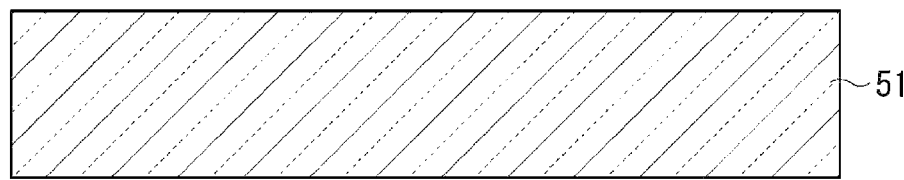
FIGS. 6A to 6F are diagrams showing a manufacturing process of the fixed substrate in the first embodiment.

First, as shown in FIG. 6A, a quartz glass substrate having a thickness dimension of 1000 μm, which is a material for manufacturing the fixed substrate 51, is prepared. Both the surfaces of the quartz glass substrate are precisely polished until surface roughness Ra of the quartz glass substrate decreases to 1 nm or less.

Thereafter, resist is applied to the surface of the fixed substrate 51 opposed to the movable substrate 52. The applied resist is exposed to light and developed by a photolithography method to pattern a place where the electrode arranging groove 511 is formed.

Figure 6B:
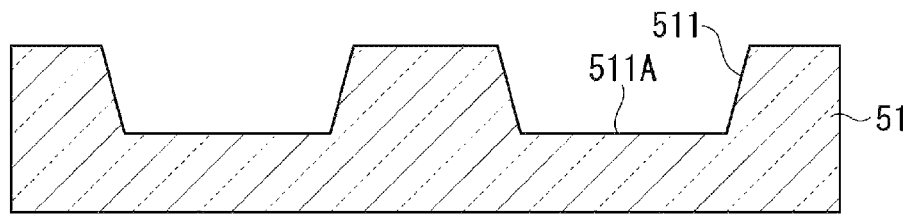

Subsequently, as shown in FIG. 6B, the electrode arranging groove 511 is etched to desired thickness. As the etching, wet etching is performed using hydrofluoric acid etchant. Thereafter, after resist for the electrode arranging groove 511 formation is removed, resist for forming the reflective-film setting section 512 is applied. A place where the reflective-film setting surface 512A is formed is patterned.

Figure 6C:
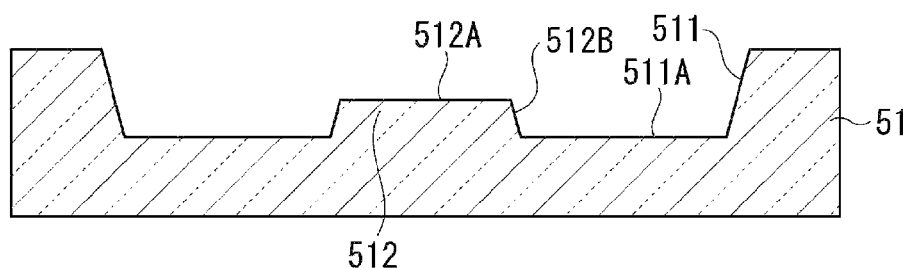

As shown in FIG. 6C, the reflective-film setting surface 512A is etched to be formed at desired height and the resist is removed. Consequently, a substrate shape of the fixed substrate 51 on which the electrode arranging groove 511 and the reflective-film setting section 512 are formed is determined.

Figure 6D:
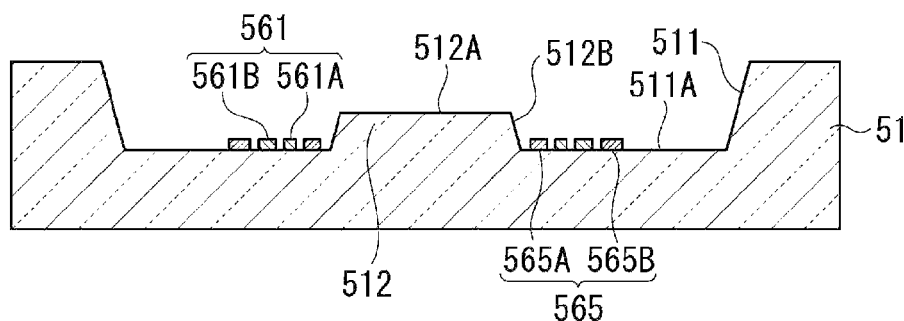

A film of an electrode material for forming the fixed electrode 561 on the fixed substrate 51 is formed. The film is patterned using the photolithography method to form the fixed electrode 561 and the fixed charging preventing electrode 565 as shown in FIG. 6D.

When an insulating layer is formed on the fixed electrode 561, after the formation of the fixed electrode 561, a film of $SiO_2$ having thickness of, for example, about 100 nm is formed over the entire surface of the fixed substrate 51 opposed to the movable substrate 52 by, for example, plasma CVD. The $SiO_2$ film on the electrode pads 563AP, 563BP, and 565P is removed by, for example, dry etching.

Figure 6E:
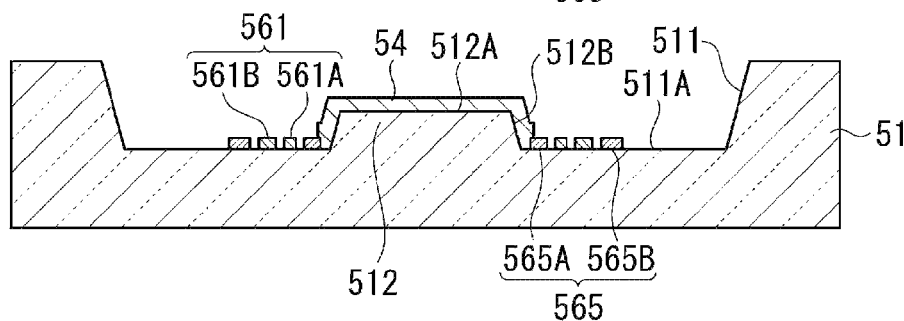

As shown in FIG. 6E, the fixed reflective film 54 is formed on the reflective-film setting surface 512A. In this embodiment, an Ag alloy is used as the fixed reflective film 54. When a metal film of Ag or the like or an alloy film of an Ag alloy or the like is used as the fixed reflective film 54, after a film layer of the fixed reflective film 54 is formed on the surface of the fixed substrate 51 on which the electrode arranging groove 511 and the reflective-film setting section 512 are formed, the film layer is patterned by the photolithography method or the like.

When a dielectric multilayer film is formed as the fixed reflective film 54, the dielectric multilayer film can be formed by, for example, a lift-off process. In this case, resist (a lift-off pattern) is formed in a portion other than a mirror forming portion on the fixed substrate 51 by the photolithography method or the like. Thereafter, a material (e.g., a dielectric multilayer film in which a high refractive layer is formed of $TiO_2$ and a low refractive layer is formed of $SiO_2$) for forming the fixed reflective film 54 is formed by a sputtering method, a vapor deposition method, or the like. After the fixed reflective film 54 is formed, the film in unnecessary portions is removed by lift-off.

Figure 6F:
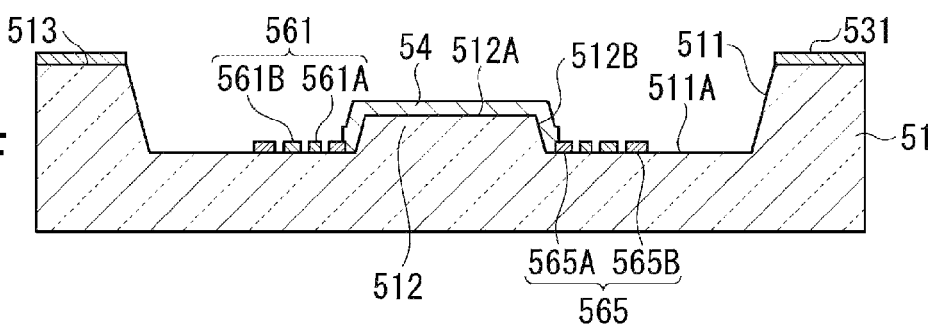

Thereafter, as shown in FIG. 6F, the plasma polymer film 531 containing polyorganosiloxane as a main component, which forms the bonding film 53, is formed on the first bonding section 513 of the fixed substrate 51 by, for example, a plasma CVD method. In a film forming process for the plasma polymer film 531, the plasma polymer film 531 is formed on the first bonding section 513 of the fixed substrate 51 using, for example, a mask opened in a position corresponding to the first bonding section 513. The thickness of the plasma polymer film 531 only has to be set to, for example, 10 nm to 1000 nm. Consequently, the fixed substrate 51 is manufactured.

5-2. Movable Substrate Manufacturing Process

Figure 7A:
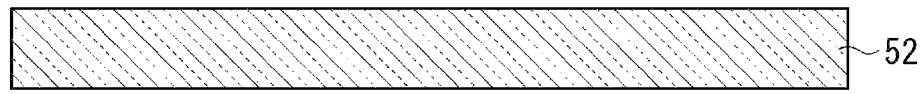
FIGS. 7A to 7E are diagrams showing a manufacturing process of the movable substrate in the first embodiment.

First, as shown in FIG. 7A, a quartz glass substrate having a thickness dimension of 600 μm, which is a material for forming the movable substrate 52, is prepared. Both the surfaces of the quartz glass substrate are precisely polished until surface roughness Ra of the quartz glass substrate decreases to 1 nm or less. Resist is applied to the entire surface of the movable substrate 52. The applied resist is exposed to light and developed by the photolithography method to pattern a place where the holding section 522 is formed.

Figure 7B:
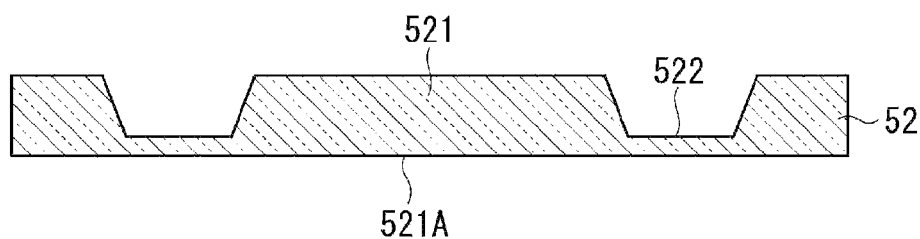

Subsequently, the quartz glass substrate is wet-etched to form the holding section 522 and the movable section 521 having thickness of, for example, 30 μm as shown in FIG. 7B. Consequently, a substrate shape of the movable substrate 52 including the movable section 521 and the holding section 522 is determined.

Figure 7C:
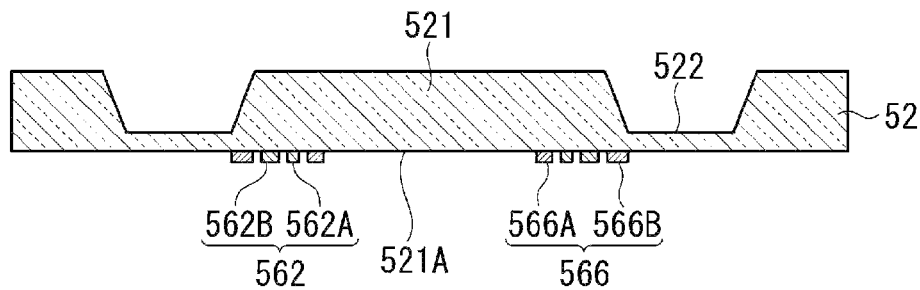

As shown in FIG. 7C, the movable electrode 562 and the movable charging preventing electrode 566 are formed along the movable surface 521A.

Specifically, like the formation of the fixed electrode 561 and the movable extracting electrode 564 on the fixed substrate 51, a film of an electrode material is formed on the movable substrate 52. The film is patterned using the photolithography method to form the movable electrode 562 and the movable extracting electrode 564.

Figure 7D:
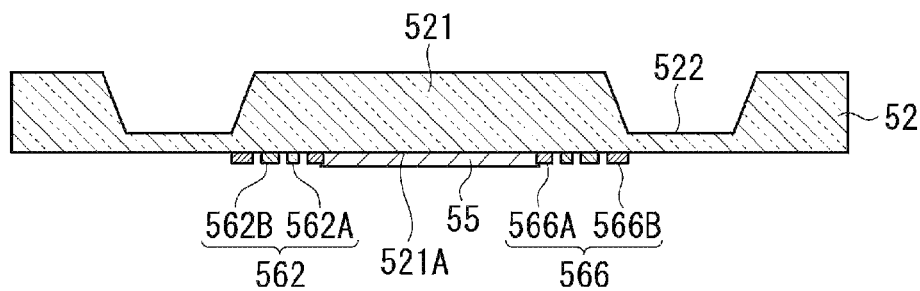

Thereafter, as shown in FIG. 7D, the movable reflective film is formed on the movable surface 521A. The movable reflective film 55 can be formed by a method same as the method of forming the fixed reflective film 54. When a metal film of Ag or the like or an alloy film of an Ag alloy or the like is used as the movable reflective film 55, after a film layer of the movable reflective film 55 is formed on the movable substrate 52, the film layer is patterned by the photolithography method or the like. As explained above, the outer circumferential portion of the movable reflective film 55 is laminated on the annular inner circumferential portion of the movable inner charging preventing electrode 566A to secure conduction of the movable reflective film 55 and the movable inner charging preventing electrode 566A. When a dielectric multilayer film is formed as the movable reflective film 55, the dielectric multilayer film can be formed by, for example, the lift-off process. In this case, for example, the movable reflective film 55 is covered with a metal film and the outer circumferential portion of the metal film is laminated on the annular inner circumferential portion of the movable inner charging preventing electrode 566A to secure conduction of the movable reflective film 55 and the movable inner charging preventing electrode 566A.

Figure 7E:
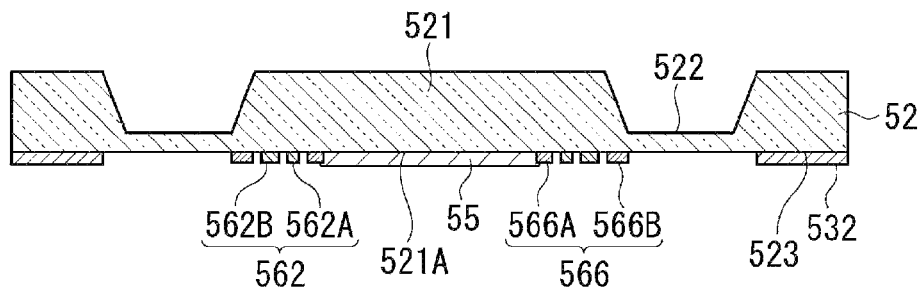

Thereafter, as shown in FIG. 7E, the plasma polymer film 532 containing polyorganosiloxane as a main component is formed on the second bonding section 523 of the movable substrate 52 by, for example, the plasma CVD method. The thickness of the plasma polymer film 532 only has to be set to, for example, 10 nm to 1000 nm.

Consequently, the movable substrate 52 is manufactured.

5-3. Bonding Process

Subsequently, the substrates formed in the fixed substrate manufacturing process and the movable substrate manufacturing process are bonded.

In this bonding process, $O_2$ plasma treatment or UV treatment is performed to give activation energy to the plasma polymer films 531 and 532 formed on the first bonding section 513 of the fixed substrate 51 and the second bonding section 523 of the movable substrate 52. The $O_2$ plasma treatment is carried out for thirty seconds under conditions of an $O_2$ flow rate of 30 cc/min, pressure of 27 Pa, and RF power of 200 W. The UV treatment is performed three minutes using excimer UV (wavelength is 172 nm) as a UV light source.

After the activation energy is given to the plasma polymer films 531 and 532, alignment of the fixed substrate 51 and the movable substrate 52 is performed to superimpose the first bonding section 513 and the second bonding section 523 via the plasma polymer films 531 and 532. At this point, the conductive member 58 is formed between the fixed charging preventing electrode pad 565P and the movable charging preventing electrode pad 566P. The fixed charging preventing electrode pad 565P and the movable charging preventing electrode pad 566P are connected by the conductive member 58 when the substrates are bonded. As the conductive member 58, Ag paste or the like may be injected from a substrate side after the formation of the wavelength variable interference filter 5.

A load of, for example, 10 kgf is applied to a bonding portion for ten minutes. Consequently, the substrates 51 and 52 are bonded.

In the manufacturing method for the wavelength variable interference filter 5 according to this embodiment, a plurality of the wavelength variable interference filters 5 are arranged in one wafer. These wavelength variable interference filters 5 are simultaneously manufactured by using the manufacturing method explained above. After the bonding process, the wavelength variable interference filters 5 are divided into a state of chips from the wafer. Thereafter, a portion of the fixed substrate 51 opposed to the movable electrode pad 564P and portions of the movable substrate 52 opposed to the fixed inner electrode pad 563AP, the fixed outer electrode pad 563BP, and the fixed charging preventing electrode pad 565P are, for example, folded to form the cutout section 514 and the cutout sections 524 and expose mounting terminal sections. Consequently, the wavelength variable interference filter 5 in a chip unit is manufactured.

6. Action and Effects of the Embodiment

In the wavelength variable interference filter 5 according to this embodiment, the fixed charging preventing electrode 565 is provided along the outer circumferential edge of the fixed electrode 561 of the fixed substrate 51. The movable charging preventing electrode 566 is provided along the outer circumferential edge of the movable electrode 562 of the movable substrate 52.

Therefore, even if charges stored in the fixed electrode 561 and the movable electrode 562 move onto the fixed substrate 51 and the movable substrate 52, it is possible to allow the charges to escape using the fixed charging preventing electrode 565 and the movable charging preventing electrode 566. It is possible to prevent charging of the fixed substrate 51 and the movable substrate 52 and charging of the fixed reflective film 54 and the movable reflective film 55. Consequently, it is possible to accurately and easily carry out adjustment of the inter-reflective film gap G1 by the electrostatic actuator 56 without taking into account a Coulomb force due to charging of the substrates and the reflective films.

The movable substrate 52 includes the movable section 521 and the holding section 522. The movable reflective film 55 and the movable electrode 562 are provided on the movable surface 521A of the movable section 521. Therefore, the film stress of the fixed reflective film 54 and the movable reflective film 55 does not act on the holding section 522, which is easily bent by an external force. It is possible to prevent a bend of the movable substrate 52 and inclination of the movable reflective film 55 in an initial state (a state in which a voltage is not applied to the electrostatic actuator 56). Further, in this embodiment, the movable inner charging preventing electrode 566A and the movable outer charging preventing electrode 566B are also provided on the movable surface 521A of the movable section 521. Therefore, it is possible to prevent a bend of the holding section 522 due to the film stress of the movable inner charging preventing electrode 566A and the movable outer charging preventing electrode 566B as well.

In this embodiment, since the outer circumferential portion of the movable reflective film 55 is laminated on the annular inner circumferential portion of the movable inner charging preventing electrode 566A, the movable inner charging preventing electrode 566A and the movable reflective film 55 are electrically connected. Since the outer circumferential portion of the fixed reflective film 54 is laminated on the annular inner circumferential portion of the fixed inner charging preventing electrode 565A, the fixed inner charging preventing electrode 565A and the fixed reflective film. 54 are electrically connected.

Therefore, it is possible to more surely prevent charging to the fixed reflective film 54 and the movable reflective film 55. Further, it is possible to suppress adhesion of floating charges and charged substances to the fixed reflective film 54 and the movable reflective film 55 as well. Since the fixed charging preventing electrode 565 and the movable charging preventing electrode 566 are grounded, the fixed reflective film 54 and the movable reflective film 55 are set to the same potential (0 potential). Consequently, it is possible to more surely prevent generation of a Coulomb force such as electrostatic attraction in the fixed reflective film 54 and the movable reflective film 55.

Second Embodiment

A second embodiment of the invention is explained with reference to the drawings.

In the first embodiment, the movable inner charging preventing electrode 566A and the movable outer charging preventing electrode 566B are provided on the movable surface 521A of the movable section 521. On the other hand, the second embodiment is different from the first embodiment in that the movable outer charging preventing electrode is formed over the entire surface of the holding section opposed to the fixed substrate.

Figure 8:
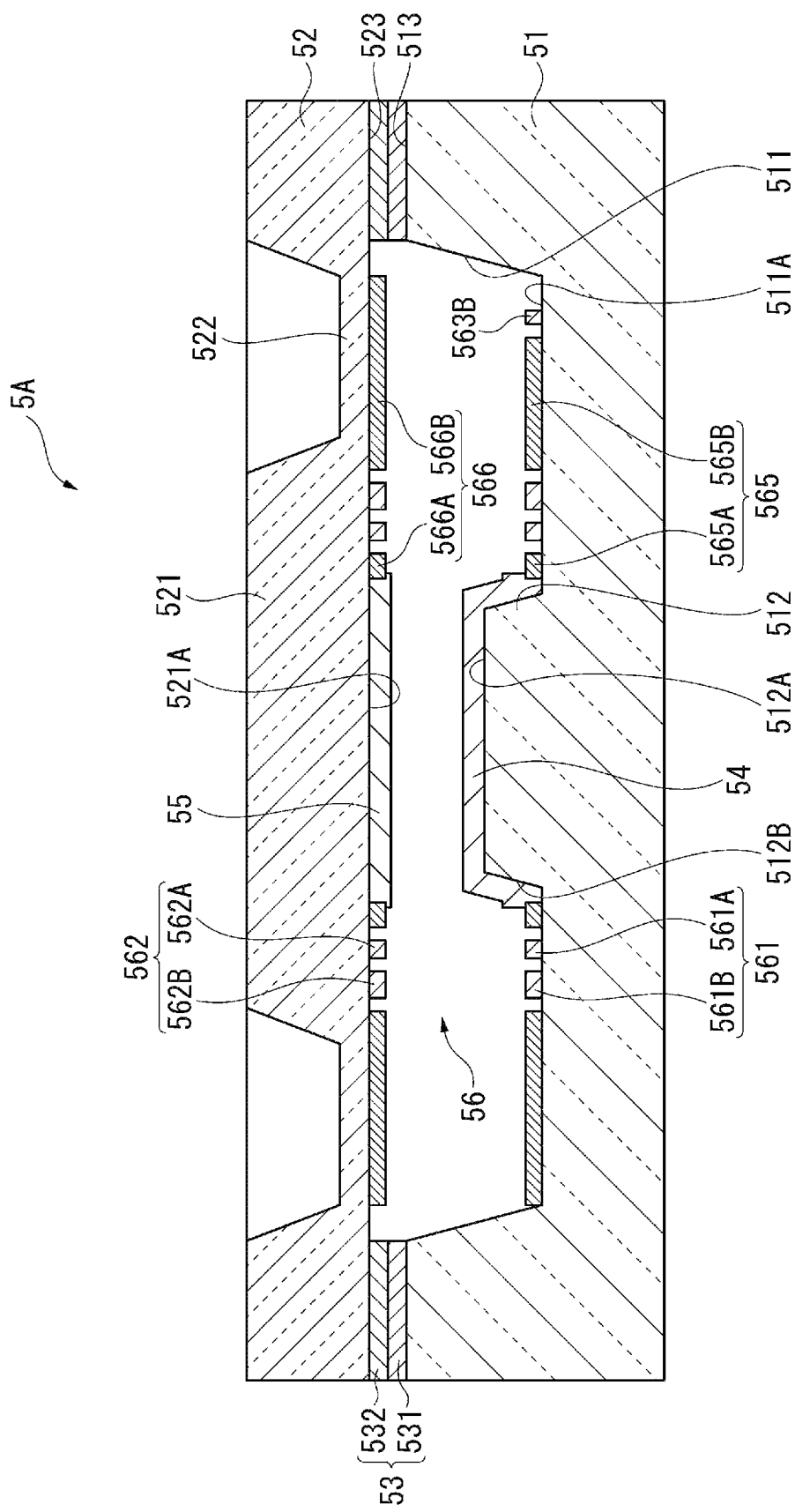
FIG. 8 is a sectional view showing a schematic configuration of a wavelength variable interference filter according to a second embodiment.
Figure 9:
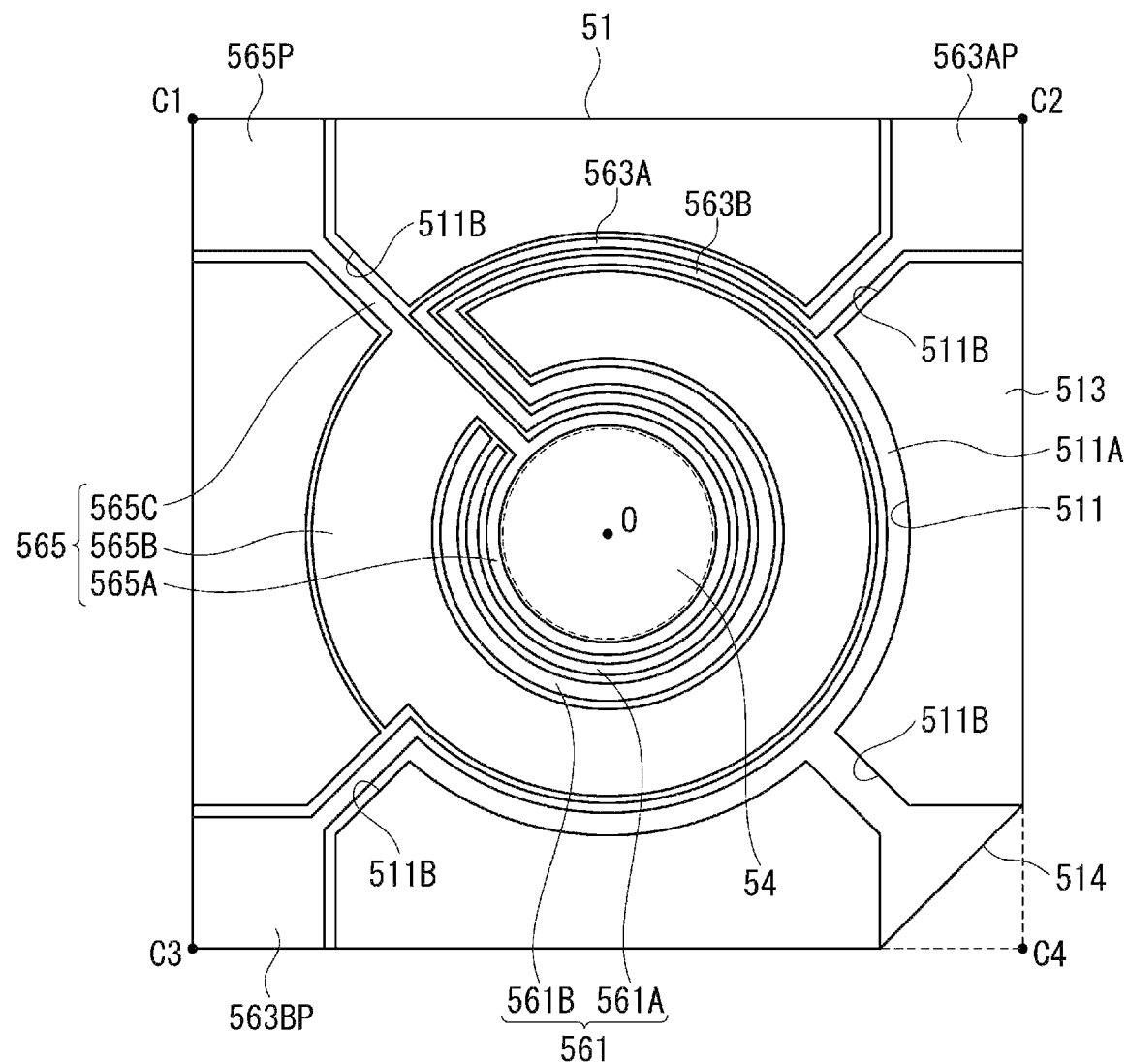
FIG. 9 is a plan view of a fixed substrate viewed from a movable substrate side in the second embodiment.
Figure 10:
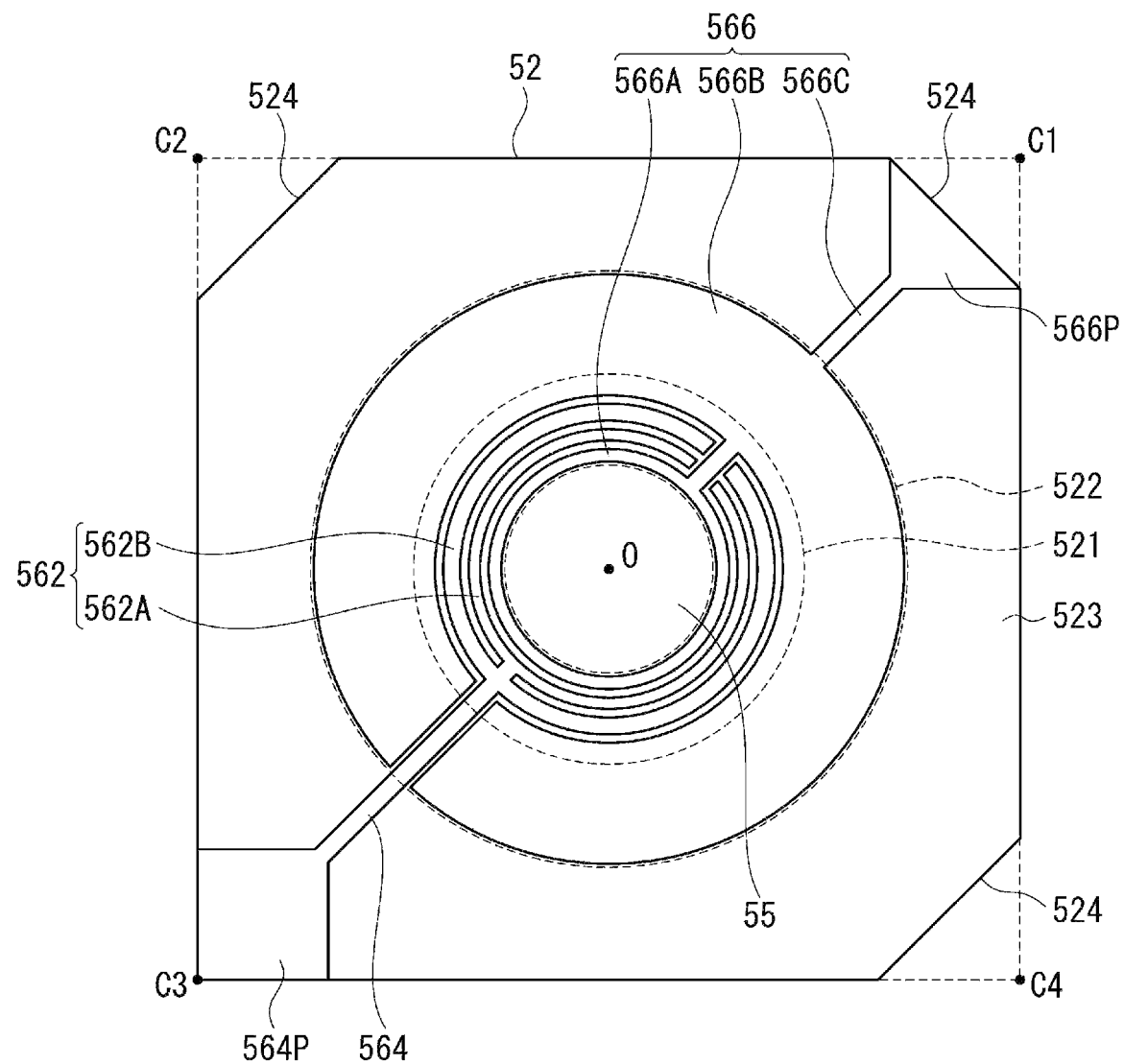
FIG. 10 is a plan view of the movable substrate viewed from the fixed substrate side in the second embodiment.

FIG. 8 is a sectional view showing a schematic configuration of a wavelength variable interference filter 5A according to the second embodiment. FIG. 9 is a plan view showing a schematic configuration of the fixed substrate 51 viewed from the movable substrate 52 side in the second embodiment. FIG. 10 is a plan view showing a schematic configuration of the movable substrate 52 viewed from the fixed substrate 51 side in the second embodiment. In the following explanation, the components already explained above are denoted by the same reference numerals and signs and explanation of the components is omitted or simplified.

In the wavelength variable interference filter 5A according to this embodiment, as shown in FIGS. 8 and 9, the fixed outer charging preventing electrode 565B of the fixed charging preventing electrode 565 is provided from a position extending along the outer circumferential edge of the fixed outer electrode 561B to a surface opposed to the holding section 522. The movable outer charging preventing electrode 566B of the movable charging preventing electrode 566 is provided from a position extending along the outer circumferential edge of the movable outer electrode 562B to the entire surface of the holding section 522 opposed to the fixed substrate 51.

In this embodiment, as shown in FIGS. 8 to 10, in the filter plan view, the outer circumferential edge of the electrode arranging groove 511 and the outer circumferential edge of the holding section 522 substantially coincide with each other. The fixed inner extracting electrode 563A and the fixed outer extracting electrode 563B are arranged in a region of the electrode setting surface 511A opposed to the holding section 522. On the other hand, for example, the electrode arranging groove 511 may be formed such that the outer circumferential edge of the electrode arranging groove 511 is located further on the diameter outer side (a side away from the plane center point O) than the outer circumferential edge of the holding section 522 in the filter plan view. In this case, the fixed outer charging preventing electrode 565B can be provided over the entire surface of the region opposed to the holdings section 522 in the electrode setting surface 511A. The fixed inner extracting electrode 563A and the fixed outer extracting electrode 563B can be arranged in the outer circumference of the fixed outer charging preventing electrode 565B. With such a configuration, it is possible to more surely prevent the influence of a Coulomb force on the holding section 522.

Action and Effects of the Second Embodiment

In the wavelength variable interference filter 5A according to the second embodiment explained above, the movable outer charging preventing electrode 566B is provided over the entire surface of the holding section 522 opposed to the fixed substrate 51. In the movable substrate 52, the holding section 522 is a portion that is bent by the action of the electrostatic attraction of the electrostatic actuator 56 and a portion easily affected by the Coulomb force when the movable section 521 is advanced and retracted with respect to the fixed substrate 51. In this embodiment, since the movable outer charging preventing electrode 566B is provided on the holding section 522, it is possible to prevent charging of the holding section 522 and effectively prevent a bend of the holding section 522 due to the Coulomb force.

The fixed outer charging preventing electrode 565B is provided in a position opposed to the movable outer charging preventing electrode 566B. Since the fixed outer charging preventing electrode 565B and the movable outer charging preventing electrode 566B are grounded, the fixed outer charging preventing electrode 565B and the movable outer charging preventing electrode 566B are maintained at zero potential.

Therefore, it is possible to prevent generation of electrostatic attraction or the like between the fixed outer charging preventing electrode 565B and the movable outer charging preventing electrode 566B and more effectively prevent a bend of the holding section 522.

Third Embodiment

A third embodiment of the invention is explained with reference to the accompanying drawings.

In the second embodiment, the movable outer charging preventing electrode 566B that covers the entire surface of the holding section 522 opposed to the fixed substrate 51 is formed. On the other hand, the third embodiment is different from the second embodiment in that the movable outer charging preventing electrode 566B includes plural openings.

Specifically, in the wavelength variable interference filter 5A according to the second embodiment, it is possible to effectively prevent charging of the holding section 522. However, it is conceivable that the holding section 522 is bent by the film stress of the movable outer charging preventing electrode 566B. On the other hand, in the third embodiment, a bend of the holding section due to the film stress of the movable outer charging preventing electrode is suppressed by providing the plural openings.

Figure 11:
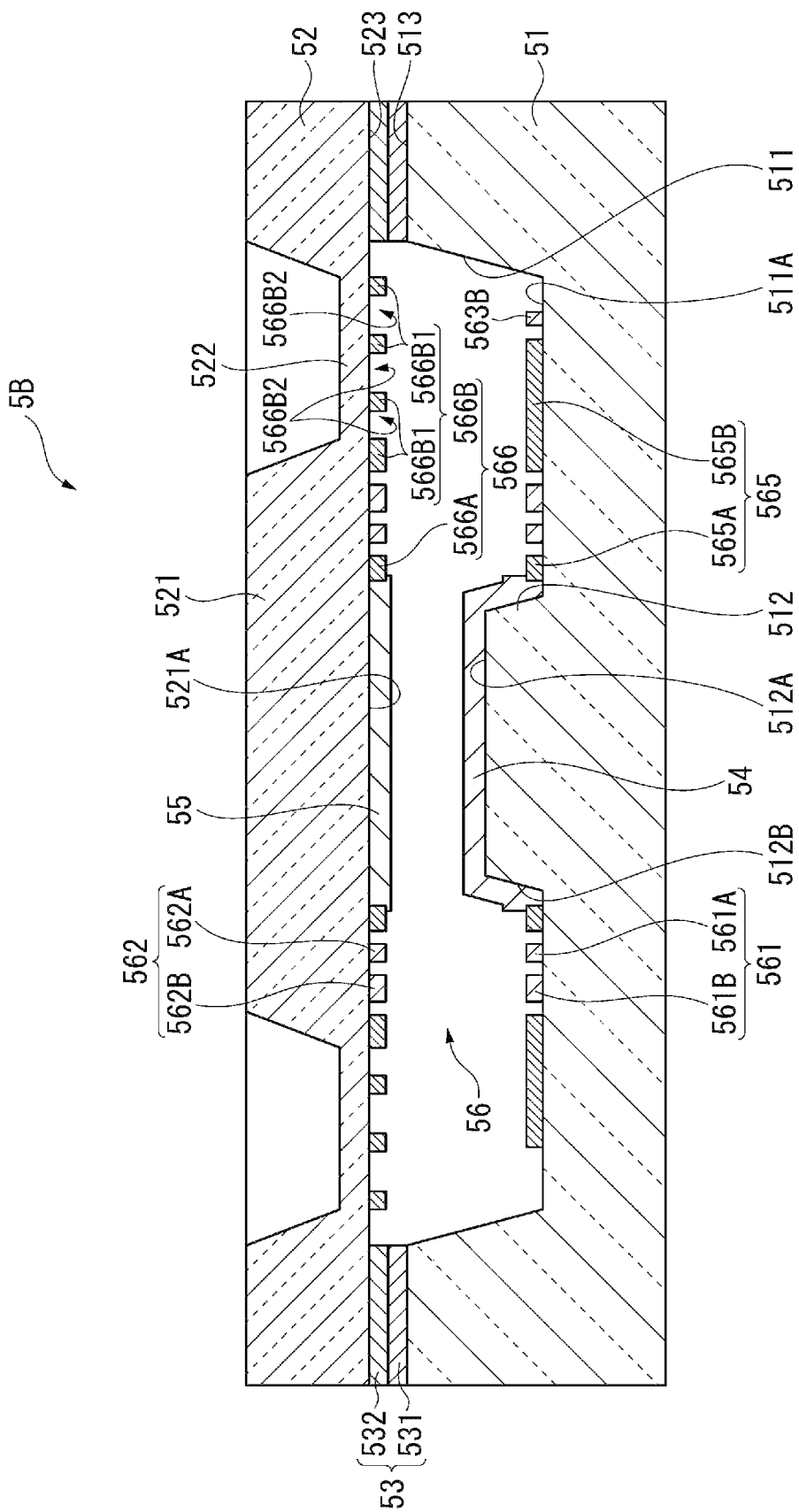
FIG. 11 is a sectional view showing a schematic configuration of a wavelength variable interference filter according to a third embodiment.
Figure 12:
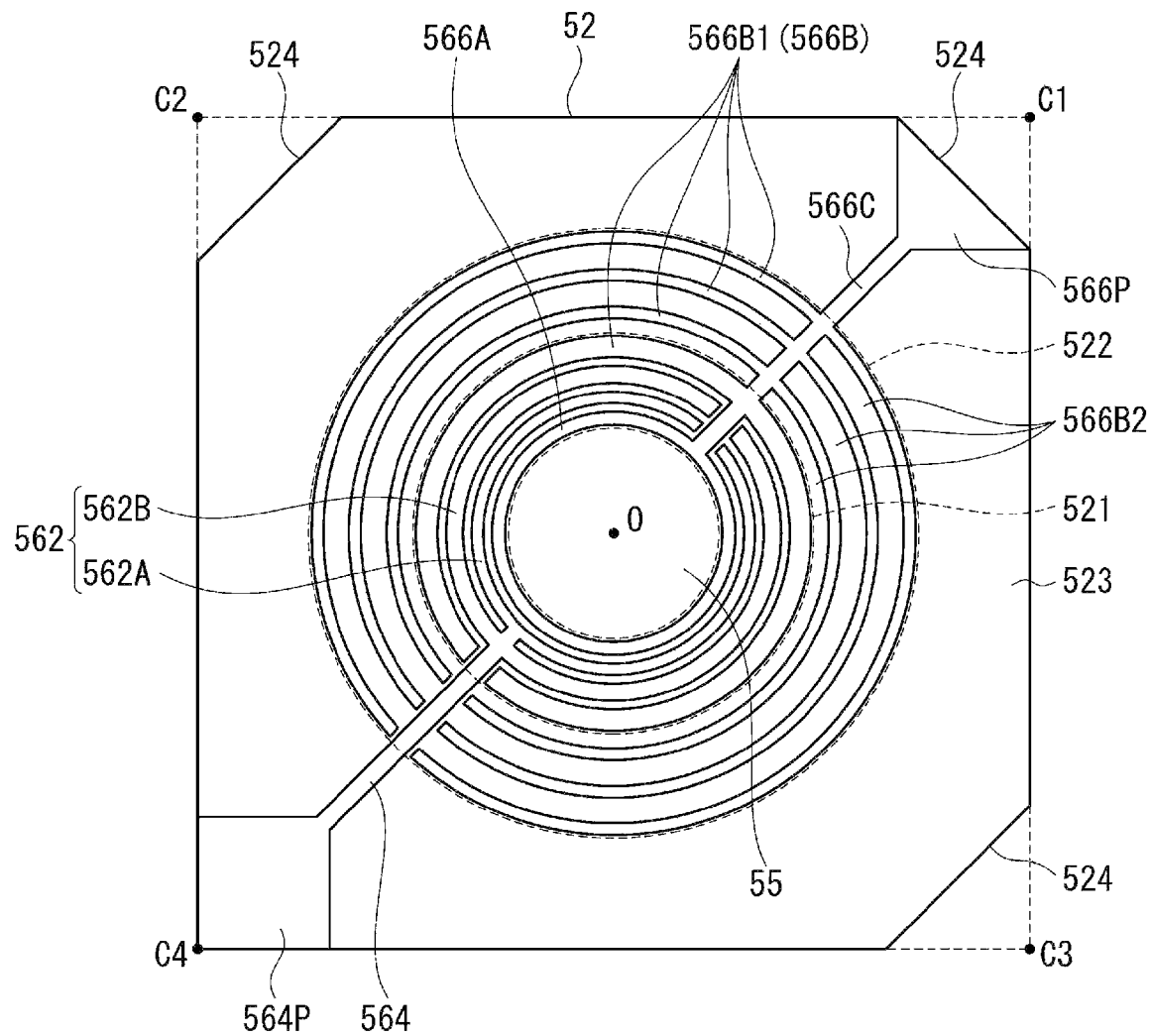
FIG. 12 is a plan view of a movable substrate viewed from a fixed substrate side in the third embodiment.

FIG. 11 is a sectional view showing a schematic configuration of a wavelength variable interference filter 5B according to the third embodiment. FIG. 12 is a plan view showing a schematic configuration of the movable substrate 52 viewed from the fixed substrate 51 side in the third embodiment. In this embodiment, since the fixed substrate 51 has a configuration same as the configuration in the second embodiment, the fixed substrate 51 is not shown in the figures and is not explained. In the wavelength variable interference filter 5B according to this embodiment, as shown in FIGS. 11 and 12, the movable outer charging preventing electrode 566B of the movable charging preventing electrode 566 is provided from a position extending along the outer circumferential edge of the movable outer electrode 562B to the entire surface opposed to the holding section 522.

The movable outer charging preventing electrode 566B includes plural C-shaped partial charging preventing electrodes 566B1. The partial charging preventing electrodes 566B1 are arranged at equal intervals on a concentric circuit having the center at the plane center point O. Specifically, openings 566B2, from which the holding section 522 is exposed, are formed among the partial charging preventing electrodes 566B1. The openings 566B2 are equally arranged on the surface of the holding section 522 opposed to the fixed substrate 51.

Action and Effects of the Third Embodiment

In the wavelength variable interference filter 5B according to the third embodiment, the movable outer charging preventing electrode 566B includes, on the surface of the holding section 522 opposed to the fixed substrate 51, the plural partial charging preventing electrodes 566B1 that form the concentric circle having the center at the plane center point O. The openings 566B2 are arranged among the partial charging preventing electrodes 566B1. With such a configuration, compared with the configuration in which the movable outer charging preventing electrode 566B that covers the entire holding section 522 is provided, it is possible to reduce the film stress of the movable outer charging preventing electrode 566B and suppress a bend of the holding section 522 due to the film stress.

Since the openings 566B2 are equally arranged, a bending balance of the holding section 522 is uniformalized. Therefore, it is possible to bend the holding section 522 in a well-balanced state when electrostatic attraction is caused to act by the electrostatic actuator 56. It is possible to maintain a parallel state of the fixed reflective film 54 and the movable reflective film 55.

In this embodiment, the plural openings 566B2 are equally arranged on the concentric circle having the center at the plane center point O. The openings 566B2 are equally arranged on the surface of the holding section 522 opposed to the fixed substrate 51. However, the wavelength variable interference filter 5B is not limited to this configuration. For example, the movable outer charging preventing electrode 566B may be formed in a mesh shape. In this case, mesh openings are equally arranged on the surface of the holding section 522 opposed to the fixed substrate 51. In this case, it is possible to prevent a bend of the holding section 522 by reducing the film stress of the movable outer charging preventing electrode 566B without losing a stress balance of the holding section 522.

Further, as the movable outer charging preventing electrode 566B, for example, plural partial charging electrodes extending in a radial shape from the plane center point O as the center may be provided. The partial charging electrodes may be arranged at equal angle intervals with respect to the plane center point O.

Fourth Embodiment

A fourth embodiment of the invention is explained with reference to the accompanying drawings.

Figure 13:
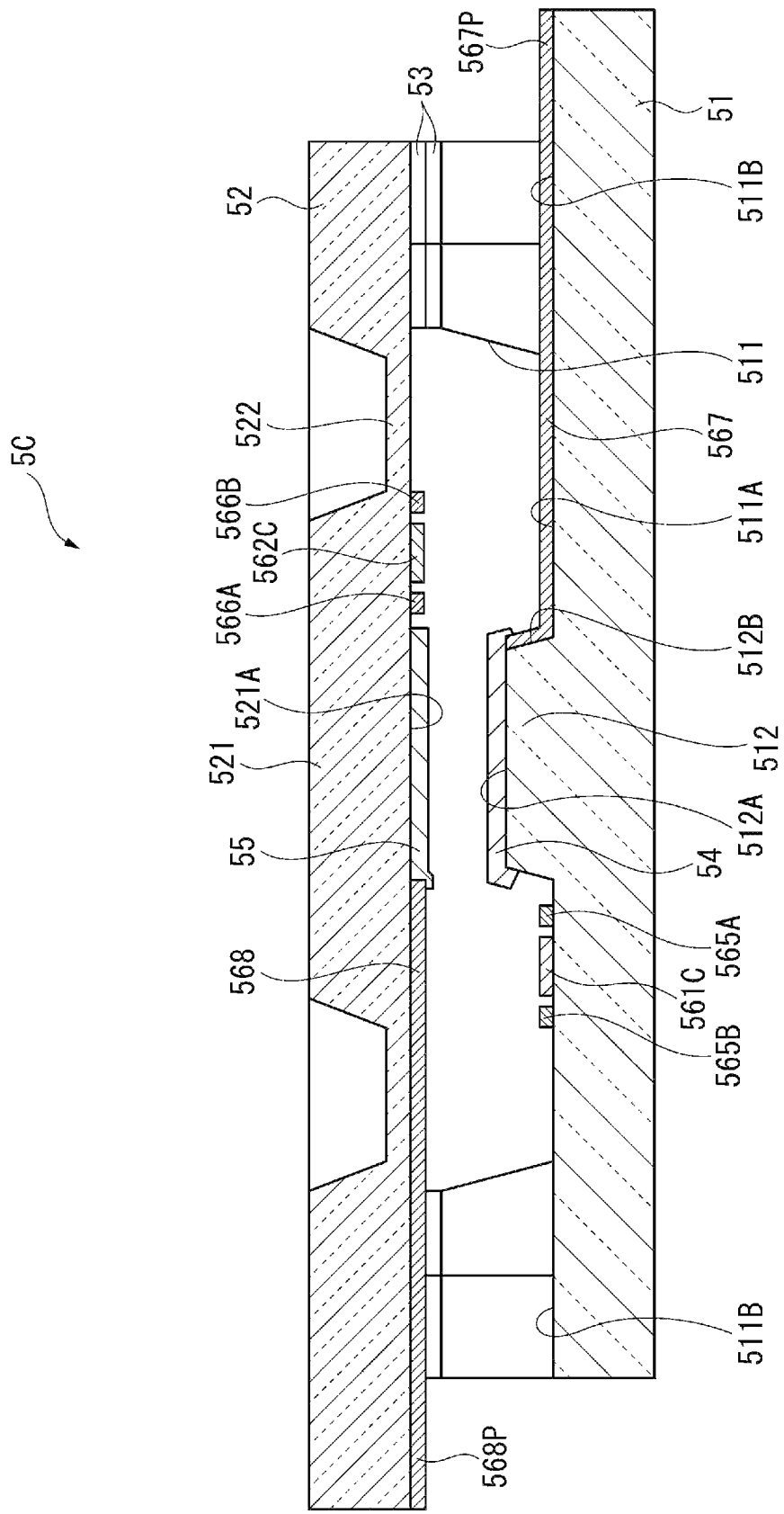
FIG. 13 is a sectional view showing a schematic configuration of a wavelength variable interference filter according to a fourth embodiment.
Figure 14:
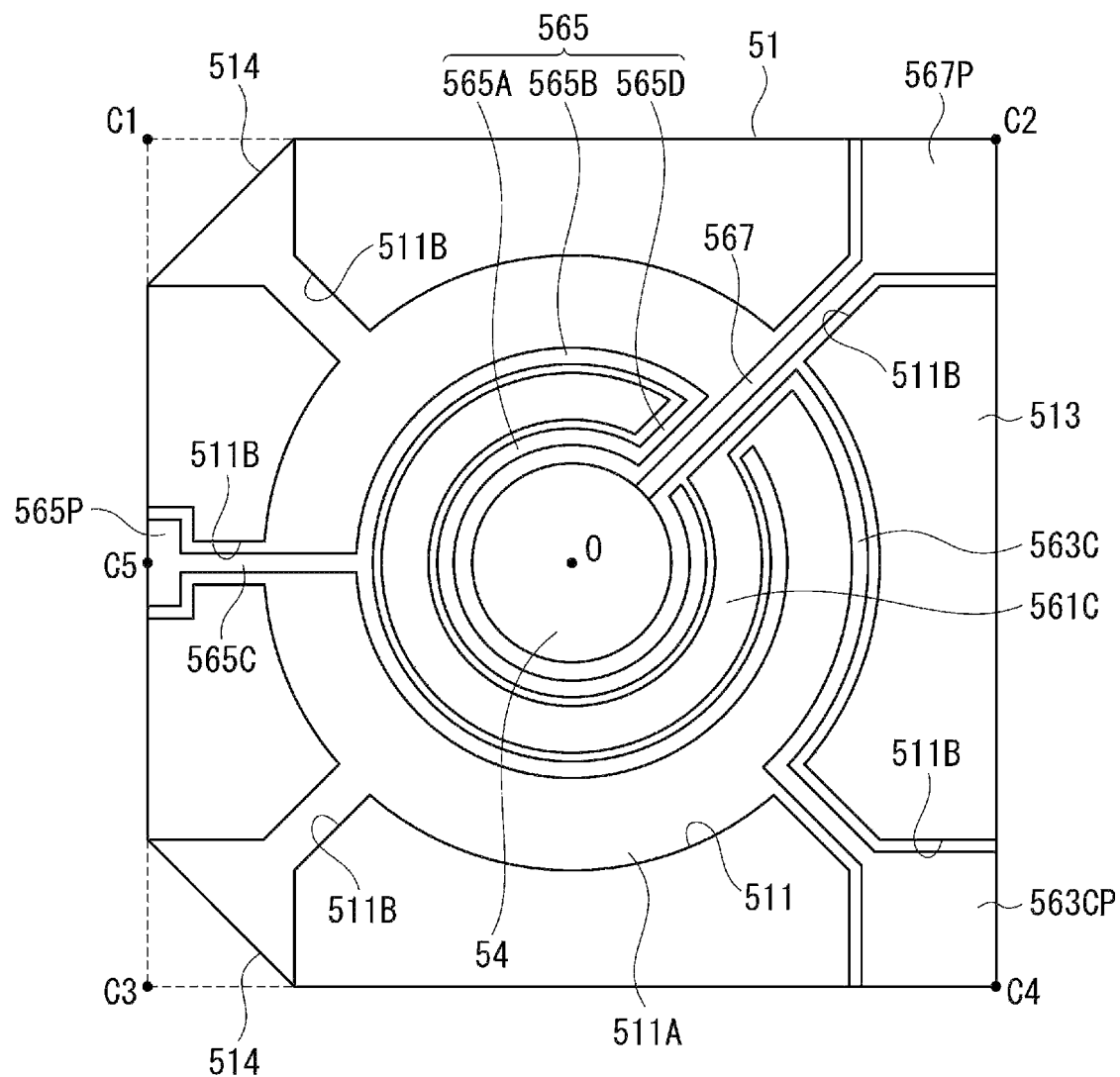
FIG. 14 is a plan view of a fixed substrate viewed from a movable substrate side in the fourth embodiment.
Figure 15:
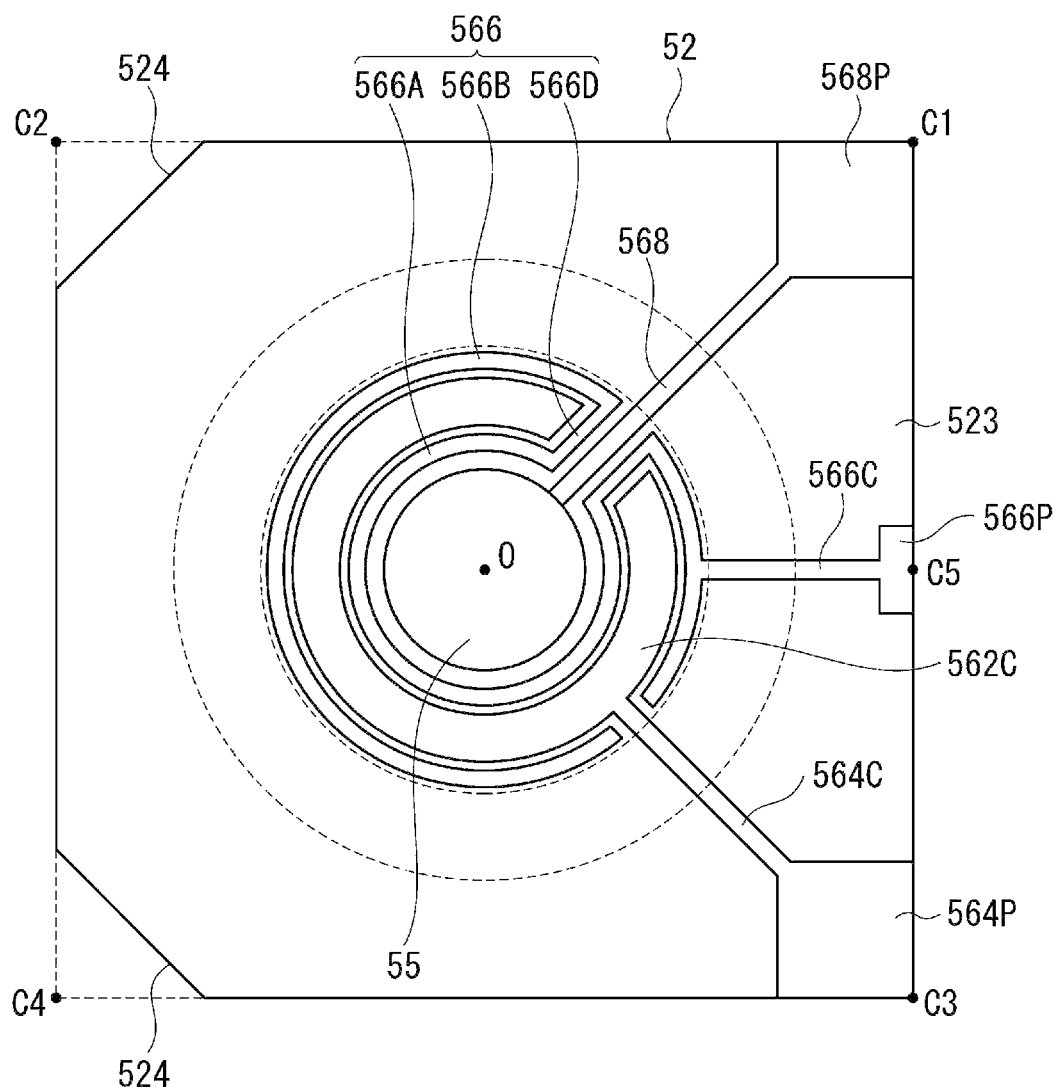
FIG. 15 is a plan view of the movable substrate viewed from the fixed substrate side according to the fourth embodiment.

In the first embodiment, the fixed inner charging preventing electrode 565A and the fixed reflective film 54 are connected and the movable inner charging preventing electrode 566A and the movable reflective film 55 are connected to maintain the fixed reflective film 54 and the movable reflective film 55 at zero potential and prevent generation of electrostatic attraction. On the other hand, the fourth embodiment is different from the first embodiment in that the fixed charging preventing electrode 565 and the movable charging preventing electrode 566 are respectively not connected to the fixed reflective film 54 and the movable reflective film 55 and a fixed capacitance detecting electrode 567 and a movable capacitance detecting electrode 568 for measuring the inter-reflective film gap G1 are respectively connected to the fixed reflective film 54 and the movable reflective film 55. FIG. 13 is a sectional view showing a schematic configuration of a wavelength variable interference filter 5C according to the fourth embodiment. FIG. 14 is a plan view of the fixed substrate 51 viewed from the movable substrate 52 side in the fourth embodiment. FIG. 15 is a plan view of the movable substrate 52 viewed from the fixed substrate 51 side in the fourth embodiment. FIG. 13 is a sectional view of the wavelength variable interference filter 5C taken along the positions of the vertex C1, the plane center point O, and the vertex C4 shown in FIGS. 14 and 15.

In the fixed substrate 51 in this embodiment, as shown in FIG. 14, the electrode extracting groove 511B extending in the direction of a middle point C5 of a side connecting the vertex C1 and the vertex C3 is formed in addition to the electrode extracting grooves 511B extending from the outer circumferential edge of the electrode arranging groove 511 to the vertexes C1, C2, C3, and C4.

In the first embodiment, the fixed electrode 561, which is a double electrode, including the fixed inner electrode 561A and the fixed outer electrode 561B is illustrated. However, in this embodiment, a single fixed electrode 561C is provided in the electrode arranging groove 511. The fixed electrode 561C is formed in a C shape having the center at the plane center point O. An opened portion of the letter C is provided, for example, in a part near the vertex C2.

On the fixed substrate 51, a fixed extracting electrode 563C extending from an end of the opened portion of the letter C of the fixed electrode 561C is provided.

As shown in FIG. 14, the fixed extracting electrode 563C extends from the end of the opened portion of the letter C of the fixed electrode 561C to the diameter outer side, extends from the end of the extension to the electrode extracting groove 511B corresponding to the vertex C4 along the outer circumferential edge of the electrode setting surface 511A, and further extends from the end of the extension to the vertex C4 along the electrode extracting groove 511B. An extension distal end (a portion located at the vertex C4 of the fixed substrate 51) of the fixed extracting electrode 563C forms a fixed electrode pad 563CP connected to the voltage control section 32. On the fixed substrate 51, the fixed capacitance detecting electrode 567 (the first detection electrode) connected to the fixed reflective film 54 provided on the reflective-film setting surface 512A is provided.

As shown in FIG. 14, the fixed capacitance detecting electrode 567 extends to the vertex C2 of the fixed substrate 51 passing through the opened portion of the letter C of the fixed electrode 561C from the outer circumferential edge of the fixed reflective film 54. An extension distal end (a portion located at the vertex C2 of the fixed substrate 51) of the fixed capacitance detecting electrode 567 forms a fixed capacitance detecting electrode pad 567P connected to a capacitance detecting section (not shown in the figures).

On the fixed substrate 51, the fixed charging preventing electrode 565 not in contact with the fixed electrode 561C and the fixed capacitance detecting electrode 567 is provided along the outer circumferential edge of the fixed electrode 561C and the outer peripheral edge of the fixed capacitance detecting electrode 567.

The fixed charging preventing electrode 565 includes the fixed inner charging preventing electrode 565A extending along the outer circumferential edge on the diameter inner side (the plane center point O side) of the fixed electrode 561C, the fixed outer charging preventing electrode 565B extending along the outer circumferential edge on the diameter outer side of the fixed electrode 561C, and a fixed connecting charging preventing electrode 565D provided in the opened portion of the letter C of the fixed electrode 561C and extending along the outer peripheral edge of the fixed capacitance detecting electrode 567. The fixed connecting charging preventing electrode 565D connects the fixed inner charging preventing electrode 565A and the fixed outer charging preventing electrode 565B.

On the fixed substrate 51, the fixed charging preventing extracting electrode 565C extending from the outer circumferential edge of the fixed outer charging preventing electrode 565B to the middle point C5 is provided. The fixed charging preventing extracting electrode 565C forms the fixed charging preventing electrode pad 565P at an extension distal end.

In this embodiment, the fixed connecting charging preventing electrode 565D is formed only in a portion of the electrode setting surface 511A opposed to the movable section 521. However, the fixed connecting charging preventing electrode 565D may be formed to extend to a portion of the electrode setting surface 511A opposed to the holding section 522. As in the second and third embodiments, the fixed outer charging preventing electrode 565B may be formed over an entire region opposed to the holding section 522.

In the movable substrate 52, as in the fixed substrate 51, a single movable electrode 562C is provided on the movable section 521. The movable electrode 562C is formed in a C-shape having the center at the plane center point O. An opened portion of the letter C is provided, for example, in a part near the vertex C1.

On the movable substrate 52, a movable extracting electrode 564C extending in the direction of the vertex C3 from the outer circumferential edge of the movable electrode 562C is provided. An extension distal end (a portion located at the vertex C3 of the movable substrate 52) of the movable extracting electrode 564C forms the movable electrode pad 564P connected to the voltage control section 32.

The movable capacitance detecting electrode 568 (the second detection electrode) connected to the movable reflective film 55 is provided on the movable substrate 52.

As shown in FIG. 15, the movable capacitance detecting electrode 568 extends to the vertex C1 of the movable substrate 52 passing through the opened portion of the letter C of the movable electrode 562C from the outer circumferential edge of the movable reflective film 55. An extension distal end (a portion located at the vertex C1 of the movable substrate 52) of the movable capacitance detecting electrode 568 forms a movable capacitance detecting electrode pad 568P connected to the capacitance detecting section (not shown in the figures). On the movable substrate 52, the movable charging preventing electrode 566 not in contact with the movable electrode 562C and the movable capacitance detecting electrode 568 is provided along the outer circumferential edge of the movable electrode 562C and the outer peripheral edge of the movable capacitance detecting electrode 568.

The movable charging preventing electrode 566 includes the movable inner charging preventing electrode 566A extending along the outer circumferential edge on the diameter inner side (the plane center point O side) of the movable electrode 562C, the movable outer charging preventing electrode 566B extending along the outer circumferential edge on the diameter outer side of the movable electrode 562C, and a movable connecting charging preventing electrode 566D provided in the opened portion of the letter C of the movable electrode 562C and extending along the outer peripheral edge of the movable capacitance detecting electrode 568. The movable connecting charging preventing electrode 566D connects the movable inner charging preventing electrode 566A and the movable outer charging preventing electrode 566B.

On the movable substrate 52, the movable charging preventing extracting electrode 566C extending from the outer circumferential edge of the movable outer charging preventing electrode 566B to the middle point C5 is provided. The movable charging preventing extracting electrode 566C forms the movable charging preventing electrode pad 566P at an extension distal end. The movable charging preventing electrode pad 566P may be connected to the fixed charging preventing electrode pad 565P by a conductive member such as Ag paste. In the example explained in this embodiment, the movable connecting charging preventing electrode 566D is formed on the movable surface 521A. However, as in the fixed substrate 51, the movable connecting charging preventing electrode 566D may be formed to extend to the holding section 522. As in the second and third embodiments, the movable outer charging preventing electrode 566B may be formed over the entire region opposed to the holding section 522.

In the wavelength variable interference filter 5C according to this embodiment explained above, it is possible to measure the dimension of the inter-reflective film gap G1 using the fixed capacitance detecting electrode 567 and the movable capacitance detecting electrode 568. In this case, a feeble fixed voltage is applied between the fixed capacitance detecting electrode 567 and the movable capacitance detecting electrode 568 and the fixed reflective film 54 and the movable reflective film 55 are caused to store charges. A charge storage amount of the fixed reflective film 54 and the movable reflective film 55 at the time when the inter-reflective film gap G1 is varied by the electrostatic actuator 56 (the fixed electrode 561 and the movable electrode 562) is measured. Consequently, it is possible to calculate the dimension of the inter-reflective film gap G1.

Action and Effects of the Fourth Embodiment

In the fourth embodiment explained above, it is possible to measure the dimension of the inter-reflective film gap G1 using the fixed capacitance detecting electrode 567 connected to the fixed reflective film 54 and the movable capacitance detecting electrode 568 connected to the movable reflective film 55. Therefore, it is possible to accurately adjust the inter-reflective film gap G1 to a desired dimension.

On the fixed substrate 51, the fixed charging preventing electrode 565 formed along the outer circumferential edge of the fixed electrode 561C and the outer peripheral edge of the fixed capacitance detecting electrode 567 is provided. On the movable substrate 52, the movable charging preventing electrode 566 formed along the outer circumferential edge of the movable electrode 562C and the outer peripheral edge of the movable capacitance detecting electrode 568 is provided. Consequently, even if charges move from the fixed electrode 561C and the fixed capacitance detecting electrode 567 to the fixed substrate 51, it is possible to allow the charges to escape using the fixed charging preventing electrode 565. Similarly, even if charges move from the movable electrode 562C and the movable capacitance detecting electrode 568 to the movable substrate 52, it is possible to allow the charges to escape using the movable charging preventing electrode 566. Therefore, as in the first to third embodiments, it is possible to prevent charging of the fixed substrate 51 and the movable substrate 52 and improve the accuracy of the adjustment of the inter-reflective film gap G1 by the electrostatic actuator 56.

Fifth Embodiment

A fifth embodiment of the invention is explained with reference to the accompanying drawings.

Figure 16:
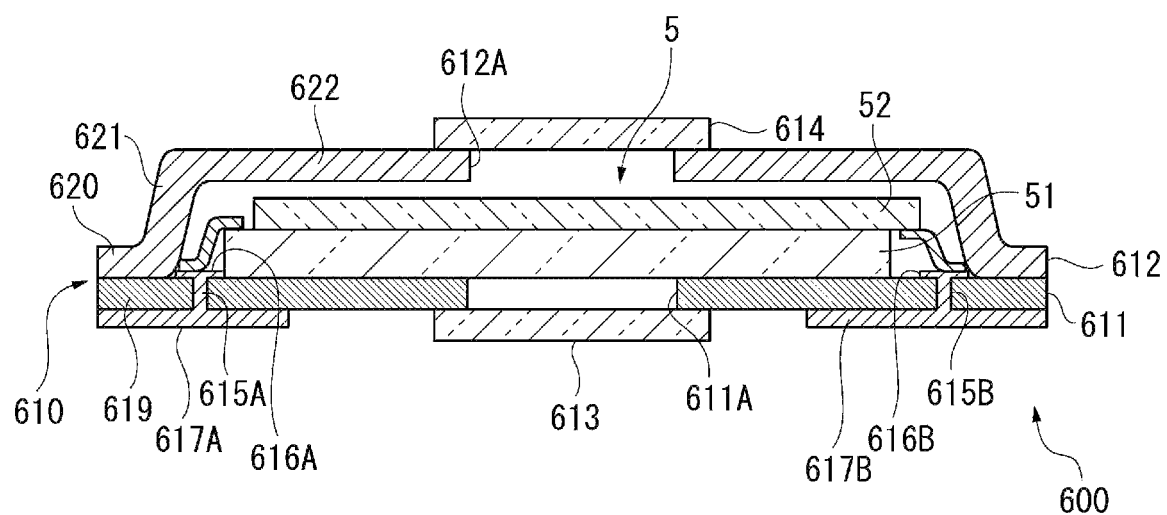
FIG. 16 is a sectional view showing a schematic configuration of an optical filter device according to a fifth embodiment.

In the colorimetric apparatus 1 according to the first embodiment, the wavelength variable interference filter 5 is directly provided in the colorimetric sensor 3, which is the optical module. In this case, the wavelength variable interference filter 5 is provided in a predetermined arrangement position provided in the colorimetric sensor 3. Wiring is carried out for the fixed inner electrode pad 563AP, the fixed outer electrode pad 563BP, the movable electrode pad 564P, and the fixed charging preventing electrode pad 565P. However, some optical module has a complicated configuration. In particular, it is sometimes difficult to directly provide the wavelength variable interference filter 5 in a small optical module. In this embodiment, an optical filter device that enables the wavelength variable interference filter 5 to be easily set even in such an optical module is explained below. FIG. 16 is a sectional view showing a schematic configuration of the optical filter device according to the fifth embodiment of the invention.

As shown in FIG. 16, an optical filter device 600 includes a housing 610 that houses the wavelength variable interference filter 5.

The housing 610 includes a bottom section 611, a lid 612, an incident side glass window 613 (a light guiding section), and an emission side glass window 614 (a light guiding section). The bottom section 611 is formed by, for example, a single layer ceramic substrate. The fixed substrate 51 of the wavelength variable interference filter 5 is fixed to the bottom section 611. On the bottom section 611, a light incident hole 611A is opened and formed in a region opposed to the reflective films 54 and 55 of the wavelength variable interference filter 5. The light incident hole 611A is a window on which incident light (inspection target light) desired to be split by the wavelength variable interference filter 5 is made incident. The incident side glass window 613 is bonded to the light incident hole 611A. As the bonding of the bottom section 611 and the incident side glass window 613, for example, glass frit bonding can be used in which glass frits, which are fragments of glass obtained by melting a glass material at high temperature and rapidly cooling the glass material, are used.

On the upper surface of the bottom section 611 (on the inner side of the housing 610), terminal sections 616 are provided in a number corresponding to the electrode pads 563AP, 563BP, 564P, and 565P of the wavelength variable interference filter 5. In the bottom section 611, through-holes 615 are formed in positions where the terminal sections 616 are provided. The terminal sections 616 are connected to connection terminals 617 provided on the lower surface of the bottom section 611 (on the outer side of the housing 610) via the through-holes 615.

A sealing section 619 bonded to the lid 612 is provided at the outer circumferential edge of the bottom section 611. The lid 612 includes, as shown in FIG. 16, a sealing section 620 bonded to the sealing section 619 of the bottom section 611, a sidewall section 621 continuous from the sealing section 620 and standing in a direction away from the bottom section 611, and a top surface section 622 continuous from the sidewall section 621 and covering the movable substrate 52 side of the wavelength variable interference filter 5. The lid 612 can be formed of an alloy such as Kovar or metal.

The sealing section 620 and the sealing section 619 of the bottom section 611 are bonded by, for example, laser sealing, whereby the lid 612 is bonded to the bottom section 611. In the top surface section 622 of the lid 612, a light emission hole 612A is opened and formed in a region opposed to the reflective films 54 and 55 of the wavelength variable interference filter 5. The light emission hole 612A is a window through which light split and extracted by the wavelength variable interference filter 5 passes. The emission side glass window 614 is bonded to the light emission hole 612A by, for example, the glass frit bonding.

In such an optical filter device 600, since the wavelength variable interference filter 5 is protected by the housing 610, it is possible to prevent breakage of the wavelength variable interference filter 5 due to an external factor. Therefore, it is possible to prevent breakage due to, for example, collision with another member when the wavelength variable interference filter 5 is set in an optical module such as a colorimetric sensor or an electronic apparatus or during maintenance.

For example, when the wavelength variable interference filter 5 manufactured in a factory is transported to an assembly line or the like for assembling the optical module or the electronic apparatus, it is possible to safely transport the wavelength variable interference filter 5 protected by the optical filter device 600.

In the optical filter device 600, the connection terminals 617 exposed to the outer circumferential surface of the housing 610 are provided. Therefore, it is possible to easily carry out wiring even when the wavelength variable interference filter 5 is incorporated in the optical module or the electronic apparatus.

Other Embodiments

The invention is not limited to the embodiments explained above. Modifications, improvements, and the like within a range in which the object of the invention can be attained are included in the invention.

For example, in the example explained in the embodiments explained above, each of the fixed charging preventing electrode 565 and the movable charging preventing electrode 566 is grounded in the voltage control section 32 to be maintained at zero potential. However, the invention is not limited to this.

Specifically, the fixed charging preventing electrode 565 and the movable charging preventing electrode 566 only have to be capable of allowing charges of the fixed electrode 561, the movable electrode 562, the fixed capacitance detecting electrode 567, the movable capacitance detecting electrode 568, and the like to escape to prevent charging of the fixed substrate 51 and the movable substrate 52. For example, as explained above, the fixed charging preventing electrode 565 and the movable charging preventing electrode 566 only have to be set to the reference potential maintained at fixed potential. The fixed charging preventing electrode 565 and the movable charging preventing electrode 566 are provided to be opposed to each other. Therefore, if the fixed charging preventing electrode 565 and the movable charging preventing electrode 566 are set to the same reference potential, a Coulomb force such as electrostatic attraction does not act between the fixed charging preventing electrode 565 and the movable charging preventing electrode 566. It is possible to prevent a bend of the movable substrate 52.

In the first to third embodiments, in order to further improve the charging preventing effect, the fixed charging preventing electrode 565 and the movable charging preventing electrode 566 may be arranged between the fixed inner electrode 561A and the fixed outer electrode 561B and between the movable inner electrode 562A and the movable outer electrode 562B as well. With such a configuration, it is possible to more effectively prevent charging of the substrates 51 and 52. By adopting such a configuration, it is possible to prevent crosstalk between the fixed inner electrode 561A and the fixed outer electrode 561B and crosstalk between the movable inner electrode 562A and the movable outer electrode 562B.

Similarly, in the configuration illustrated in the fourth embodiment, the fixed connecting charging preventing electrode 565D and the movable connecting charging preventing electrode 566D are arranged along one side edges of the fixed capacitance detecting electrode 567 and the movable capacitance detecting electrode 568. However, the fixed connecting charging preventing electrode 565D and the movable connecting charging preventing electrode 566D may be provided along both side edges of the fixed capacitance detecting electrode 567 and the movable capacitance detecting electrode 568.

In the configurations illustrated in the first to fourth embodiments, the fixed charging preventing electrode 565 and the movable charging preventing electrode 566 are arranged along the outer circumferential edges of the fixed electrode 561 and the movable electrode 562, which are caused to function as the electrostatic actuators, and the fixed capacitance detecting electrode 567 and the movable capacitance detecting electrode 568, which are caused to function as the capacitive electrodes. However, the invention is not limited to this. For example, when the temperature sensor is provided in the wavelength variable interference filter 5 in order to suppress a bend corresponding to a temperature change of the wavelength variable interference filter 5, the fixed charging preventing electrode 565 and the fixed capacitance detecting electrode 567 may be provided along the outer circumference of a wiring electrode to the temperature sensor.

The wavelength variable interference filters 5, 5A, 5B, and 5C illustrated in the embodiments cause light made incident from the fixed substrate 51 side to interfere between the fixed reflective film 54 and the movable reflective film 55 and emit extracted light from the movable substrate 52 side. However, the invention is not limited to this.

For example, the light extracted by the light interference between the fixed reflective film 54 and the movable reflective film 55 may be emitted to the fixed substrate 51 side again. In this case, a non-translucent member may be used as the movable substrate 52.

In the configuration explained in the embodiments, the dimension of the inter-electrode gap G2 is larger than the dimension of the inter-reflective film gap G1. However, the invention is not limited to this. For example, depending on a selected wavelength range or the like of light extracted by the wavelength variable interference filters 5, 5A, 5B, and 5C, the dimension of the inter-reflective film gap G1 may be larger than the dimension of the inter-electrode gap G2. For example, when light other than a near infrared ray having large wavelength is filtered by the wavelength variable interference filter, it is conceivable to set the inter-reflective film gap G1 larger than the inter-electrode gap G2.

The colorimetric apparatus 1 is illustrated as the electronic apparatus in the embodiment of the invention. However, besides, the wavelength variable interference filter, the optical module, and the electronic apparatus in the embodiment of the invention can be used in various fields.

For example, the wavelength variable interference filter, the optical module, and the electronic apparatus can be used as a system of an optical base for detecting the presence of a specific substance. As such a system, a gas detecting apparatus can be illustrated, such as a vehicle-mounted gas leakage detector that adopts a spectroscopic measurement method in which the wavelength variable interference filter in the embodiment of the invention is used and detects a specific gas at high sensitivity or an optoacoustic rare gas detector for exhalation check.

An example of such a gas detecting apparatus is explained below with reference to the accompanying drawings.

Figure 17:
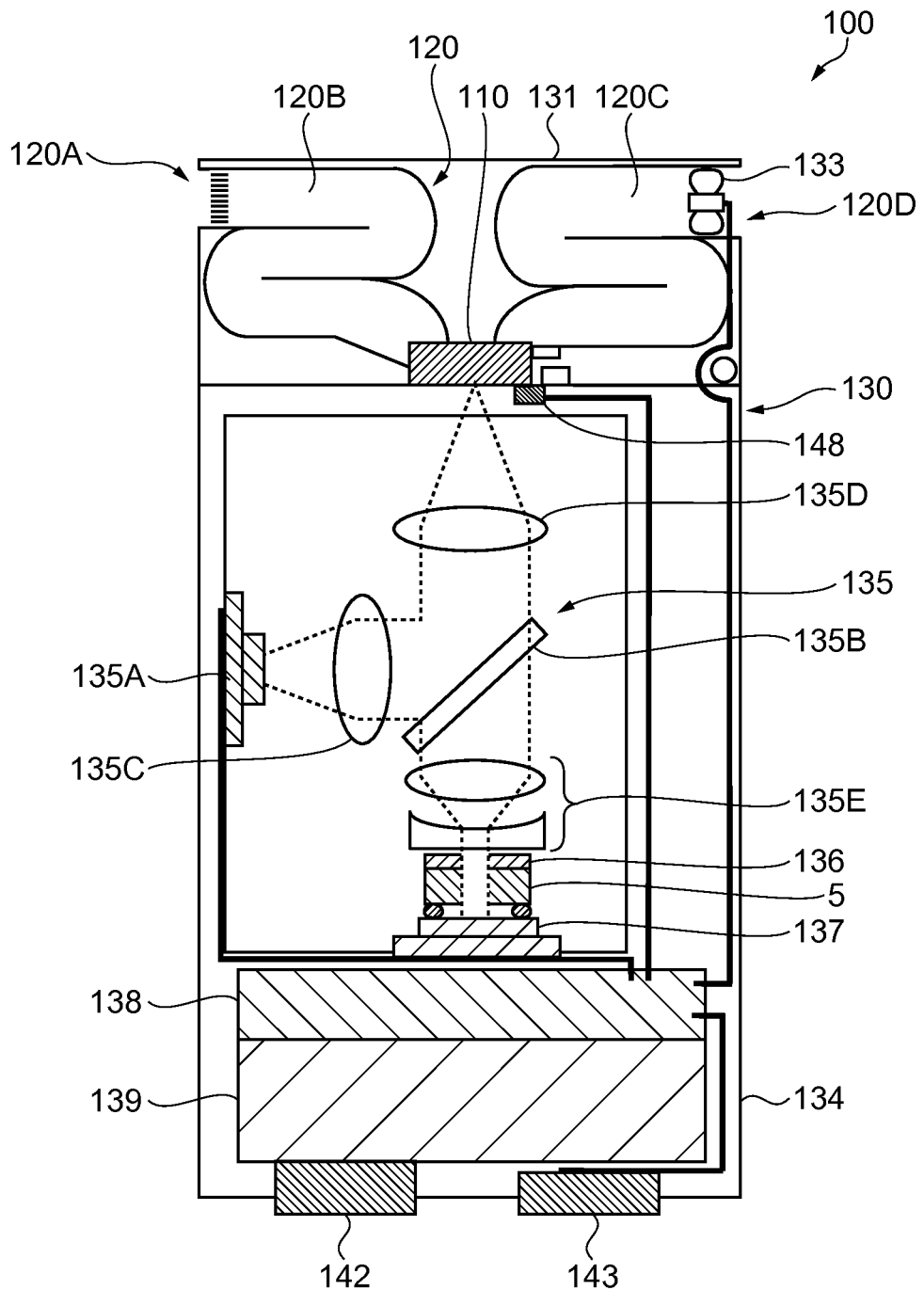
FIG. 17 is a schematic diagram showing a gas detecting apparatus including a wavelength variable interference filter in another embodiment.

FIG. 17 is a schematic diagram showing an example of the gas detecting apparatus including the wavelength variable interference filter.

Figure 18:
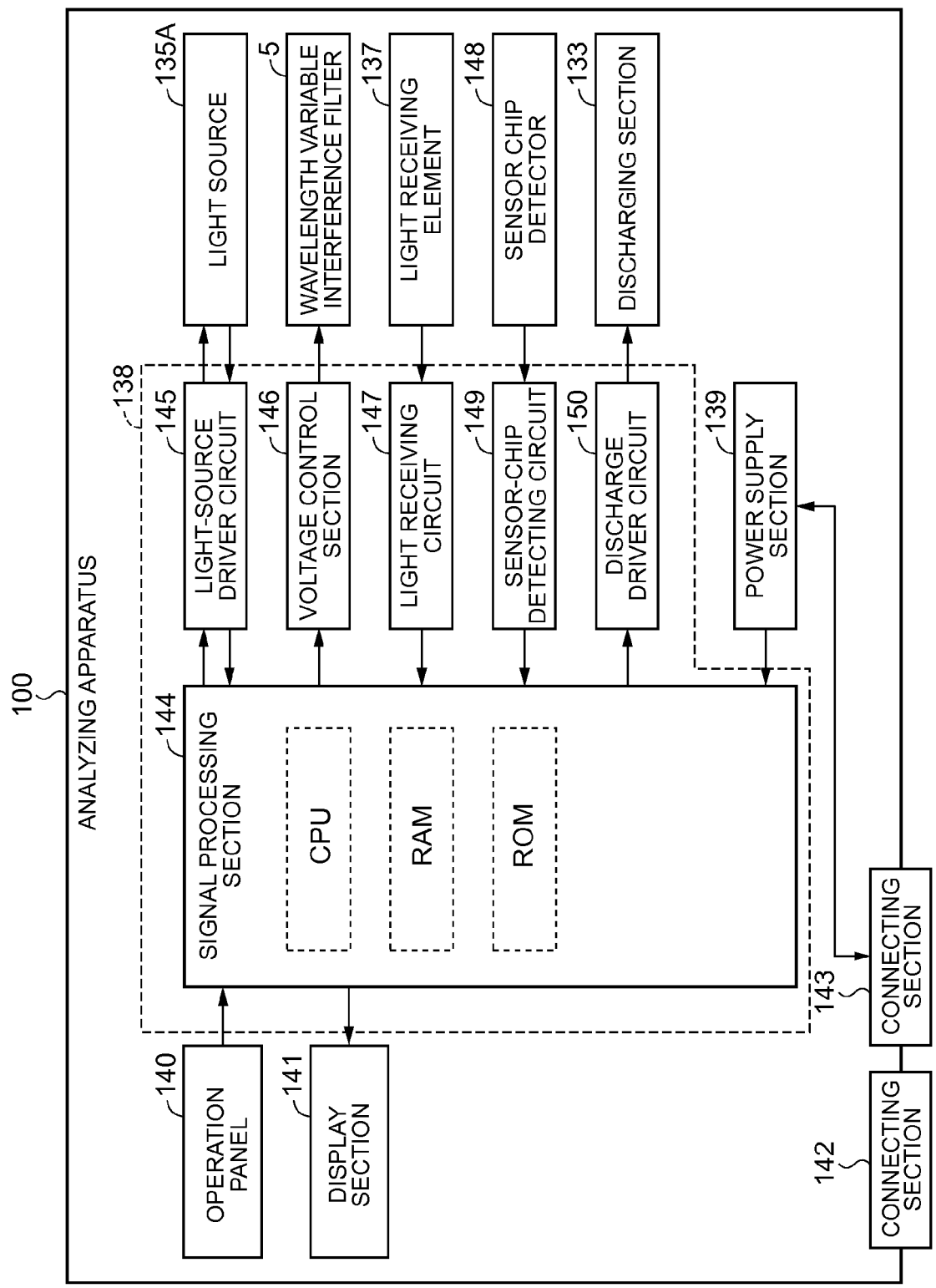
FIG. 18 is a block diagram showing the configuration of a control system of the gas detecting apparatus shown in FIG. 17.

FIG. 18 is a block diagram showing the configuration of a control system of the gas detecting apparatus shown in FIG. 17.

A gas detecting apparatus 100 includes, as shown in FIG. 17, a sensor chip 110, a channel 120 including a suction port 120A, a suction channel 120B, a discharge channel 120C, and a discharge port 120D, and a main body section 130.

The main body section 130 includes a detecting device (an optical module) including a sensor section cover 131 including an opening through which the channel 120 can be attached and detached, a discharging section 133, a housing 134, an optical section 135, a filter 136, the wavelength variable interference filter 5, and a light receiving element 137 (a detecting section), a control section 138 that processes a detected signal and controls the detecting section, and a power supply section 139 that supplies electric power. The optical section 135 includes a light source 135A that emits light, a beam splitter 135B that reflects the light made incident from the light source 135A to the sensor chip 110 side and transmits light made incident from the sensor chip 110 side to the light receiving element 137 side, and lenses 135C, 135D, and 135E. A configuration including the wavelength variable interference filter 5 is illustrated. However, a configuration including the wavelength variable interference filter 5A, 5B, or 5C may be adopted.

As shown in FIG. 18, an operation panel 140, a display section 141, a connecting section 142 for interface with the outside, and the power supply section 139 are provided on the surface of the gas detecting apparatus 100. When the power supply section 139 is a secondary battery, the gas detecting apparatus 100 may include a connecting section 143 for charging. Further, the control section 138 of the gas detecting apparatus 100 includes, as shown in FIG. 18, a signal processing section 144 including a CPU, a light-source driver circuit 145 for controlling the light source 135A, a voltage control section 146 for controlling the wavelength variable interference filter 5, a light receiving circuit 147 that receives a signal from the light receiving element 137, a sensor-chip detecting circuit 149 that receives a signal from a sensor chip detector 148 that reads a code of the sensor chip 110 and detects presence or absence of the sensor chip 110, and a discharge driver circuit 150 that controls the discharging section 133. The operation of the gas detecting apparatus 100 explained above is explained below.

The sensor chip detector 148 is provided on the inside of the sensor section cover 131 in an upper part of the main body section 130. The sensor chip detector 148 detects presence or absence of the sensor chip 110. When the signal processing section 144 detects a detection signal from the sensor chip detector 148, the signal processing section 144 determines that the sensor chip 110 is mounted. The signal processing section 144 outputs, to the display section 141, a display signal for causing the display section 141 to display a message that a detecting operation can be carried out.

When the operation panel 140 is operated by, for example, a user and an instruction signal for instructing a start of detection processing is output from the operation panel 140 to the signal processing section 144, first, the signal processing section 144 outputs a signal for light source actuation to the light-source driver circuit 145 and actuates the light source 135A. When the light source 135A is driven, the light source 135A emits a stable laser beam having single wavelength and linear polarization. The light source 135A incorporates a temperature sensor and a light amount sensor.

Information of the temperature sensor and the light amount sensor is output to the signal processing section 144. When the signal processing section 144 determines, on the basis of temperature and a light amount input from the light source 135A, that the light source 135A is stably operating, the signal processing section 144 controls the discharge driver circuit 150 to actuate the discharging section 133. Consequently, a gas sample containing a target substance (gas molecule) that should be detected is guided from the suction port 120A to the suction channel 120B, the inside of the sensor chip 110, the discharge channel 120C, and the discharge port 120D.

The sensor chip 110 is a sensor that incorporates plural metal nano-structures and makes use of localized surface plasmon resonance. In such a sensor chip 110, a reinforced electric field is formed among the metal nano-structures by a laser beam. When the gas molecule intrudes into the reinforced electric field, Raman scattering light and Rayleigh scattering light including information concerning molecule oscillation are generated.

The Raman scattering light and the Rayleigh scattering light are made incident on the filter 136 through the optical section 135. The Rayleigh scattering light is separated by the filter 136. The Raman scattering light is made incident on the wavelength variable interference filter 5. The signal processing section 144 controls the voltage control section 146, adjusts a voltage applied to the wavelength variable interference filter 5, and causes the wavelength variable interference filter 5 to split the Raman scattering light corresponding to a detection target gas molecule. Thereafter, when the split light is received by the light receiving element 137, the light receiving element 137 outputs alight reception signal corresponding to a received light amount to the signal processing section 144 via the light receiving circuit 147. The signal processing section 144 compares spectrum data of the Raman scattering light corresponding to the detection target gas molecule obtained as explained above and data stored in a ROM, determines whether the gas molecule is a target gas molecule, and specifies a substance. The signal processing section 144 causes the display section 141 to display information concerning a result of the specification of the substance or outputs the information to the outside from the connecting section 142.

In FIGS. 17 and 18, the gas detecting apparatus 100 is illustrated that splits the Raman scattering light using the wavelength variable interference filter 5 and performs gas detection from the split Raman scattering light. However, as the gas detecting apparatus, a gas detecting apparatus that specifies a gas type by detecting absorbance peculiar to gas may be used. In this case, a gas sensor that causes the gas to flow into a sensor and detects light absorbed by the gas in incident light is used as the optical module in the embodiment of the invention. A gas detecting apparatus that analyzes and discriminates the gas caused to flow into the sensor by such a gas sensor is the electronic apparatus in the embodiment of the invention. With such a configuration, it is possible to detect a component of gas using the wavelength variable interference filter in the embodiment of the invention.

The system for detecting the presence of a specific substance is not limited to the system for detecting gas explained above. As the system, a substance component analyzing apparatus such as a noninvasive measuring apparatus for a saccharide by near infrared ray spectroscopy or a noninvasive measuring apparatus for information concerning foods, organisms, minerals, and the like can be illustrated.

A food analyzing apparatus is explained below as an example of the substance component analyzing apparatus.

Figure 19:
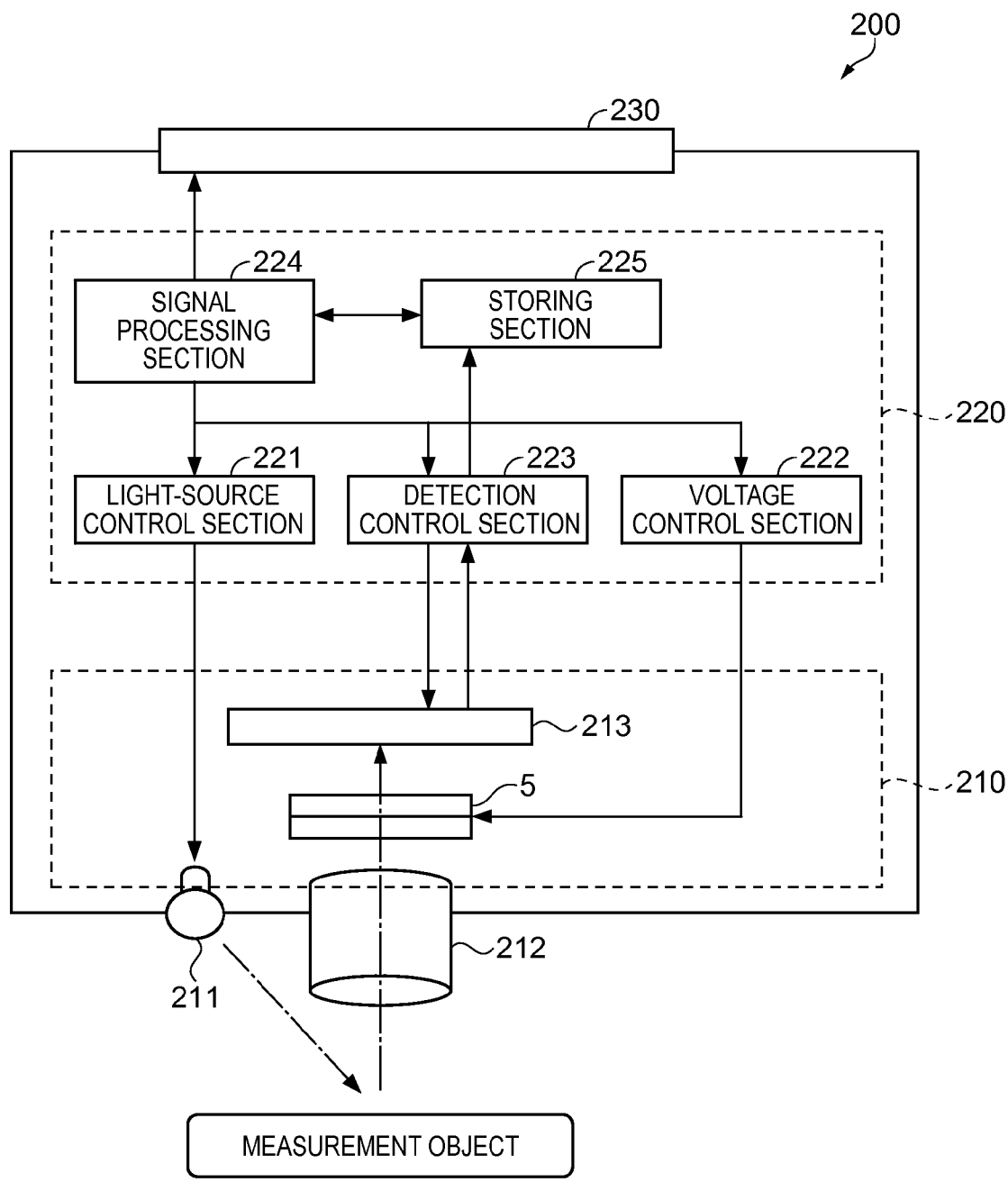
FIG. 19 is a diagram showing a schematic configuration of a food analyzing apparatus including a wavelength variable interference filter in another embodiment.

FIG. 19 is a diagram showing a schematic configuration of the food analyzing apparatus, which is an example of an electronic apparatus in which the wavelength variable interference filter 5 is used. Although the wavelength variable interference filter 5 is used, the wavelength variable interference filter 5A, 5B, or 5C may be used.

A food analyzing apparatus 200 includes, as shown in FIG. 19, a detector 210 (an optical module), a control section 220, and a display section 230. The detector 210 includes a light source 211 that emits light, an image pickup lens 212 into which light from a measurement object is led, the wavelength variable interference filter 5 that splits the light led in from the image pickup lens 212, and an image pickup section 213 (a detecting section) that detects the split light.

The control section 220 includes a light-source control section 221 that carries out control for turning on and off the light source 211 and brightness control while the light source 211 is on, a voltage control section 222 that controls the wavelength variable interference filter 5, a detection control section 223 that controls the image pickup section 213 and acquires a split light image picked up by the image pickup section 213, a signal processing section 224, and a storing section 225.

In the food analyzing apparatus 200, when the system is driven, the light-source control section 221 controls the light source 211. The light source 211 irradiates light on the measurement object. The light reflected by the measurement object is made incident on the wavelength variable interference filter 5 through the image pickup lens 212. A voltage enough for splitting predetermined wavelength is applied to the wavelength variable interference filter 5 according to the control by the voltage control section 222. The image pickup section 213 including a CCD camera picks up an image of the split light. The storing section 225 accumulates the picked-up light image as a split-light image. The signal processing section 224 controls the voltage control section 222 to change a voltage value applied to the wavelength variable interference filter 5 and acquires split-light images corresponding to respective wavelengths.

The signal processing section 224 subjects data of pixels in the images accumulated in the storing section 225 to arithmetic processing and calculates spectra in the pixels. In the storing section 225, for example, information concerning ingredients of foods corresponding to spectra is stored. The signal processing section 224 analyzes data of the calculated spectra on the basis of the information concerning foods stored in the storing section 225 and calculates food ingredients included in a detection target and contents of the food ingredients. It is also possible to calculate food calories, freshness, and the like from the calculated food ingredients and contents. Further, it is also possible to carry out, for example, extraction of a portion where freshness is deteriorated in the detection target food by analyzing a spectrum distribution in the images. Moreover, it is also possible to carry out detection of, for example, foreign matters included in the food.

The signal processing section 224 performs processing for causing the display section 230 to display information concerning the ingredients, the contents, the calories, the freshness, and the like of the detection target food obtained as explained above.

In FIG. 19, the example of the food analyzing apparatus 200 is shown. However, with a substantially the same configuration, the electronic apparatus can be used as the noninvasive measuring apparatus for the other information explained above as well. For example, the electronic apparatus can be used as an organism analyzing apparatus that performs an analysis of organism components such as measurement and analysis of body fluid components of blood or the like. As such an organism analyzing apparatus, for example, as an apparatus that measures body fluid components of blood or the like, an apparatus that detects ethyl alcohol can be used as an apparatus for drunken driving prevention that detects a drunken state of a driver. The electronic apparatus can be used as an electronic endoscope system including such an organism analyzing apparatus as well.

Further, the electronic apparatus can be used as a mineral analyzing apparatus that carries out a component analysis for minerals.

Furthermore, as the wavelength variable interference filter, the optical module, and the electronic apparatus in the embodiment of the invention, apparatuses explained below can be applied.

For example, it is also possible to transmit data with lights having respective wavelengths by changing the intensities of the lights having the respective wavelengths over time. In this case, data transmitted by light having specific wavelength can be extracted by splitting the light having the specific wavelength with the wavelength variable interference filter provided in the optical module to cause a light receiving section to receive the light. Optical communication can also be carried out by processing data of the lights having the respective wavelengths using the electronic apparatus including the optical module for data extraction.

Figure 20:
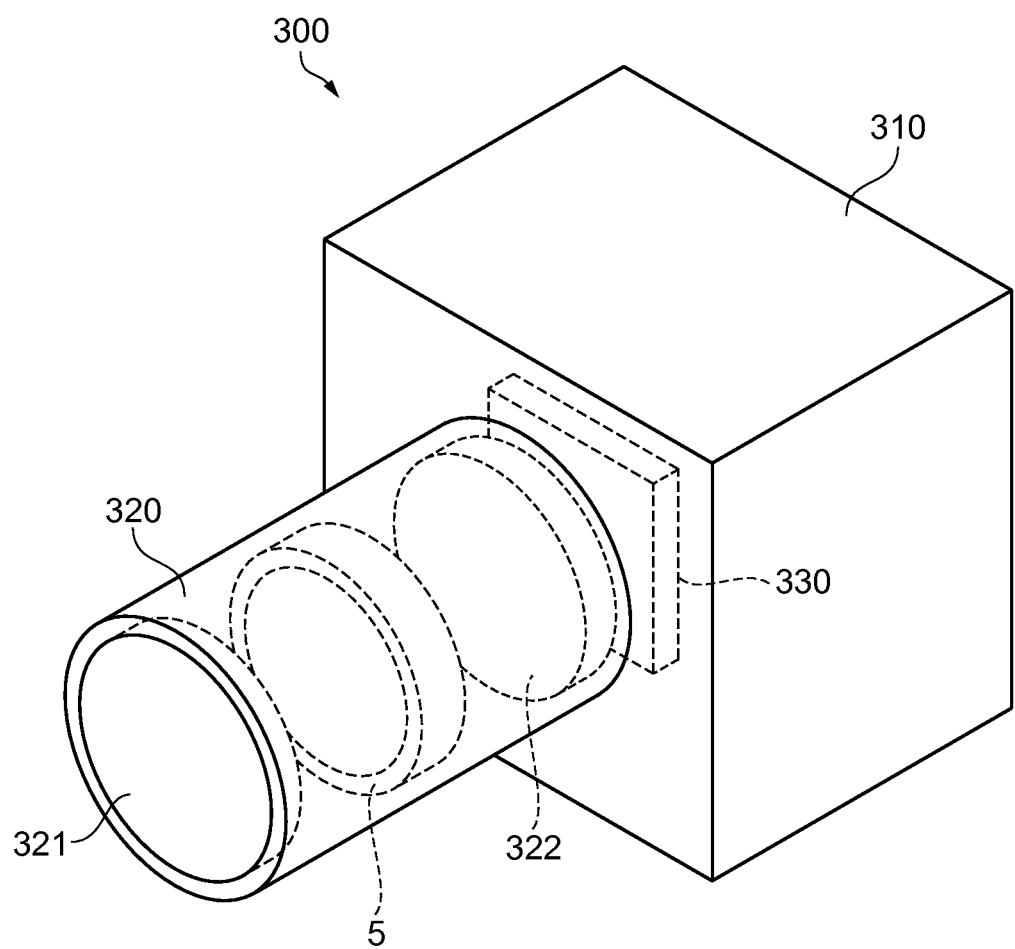
FIG. 20 is a schematic diagram showing a schematic configuration of a spectrum camera in another embodiment.

The electronic apparatus can be applied to a spectral camera, a spectral analyzer, and the like that pick up a spectral image by splitting light using the wavelength variable interference filter in the embodiment of the invention. As an example of such a spectrum camera, there is an infrared camera incorporating the wavelength variable interference filter. FIG. 20 is a schematic diagram showing a schematic configuration of the spectral camera. A spectral camera 300 includes, as shown in FIG. 20, a camera main body 310, an image pickup lens unit 320, and an image pickup section 330 (a detecting section).

The camera main body 310 is a portion gripped and operated by a user.

The image pickup lens unit 320 is provided in the camera main body 310. The image pickup lens unit 320 guides incident image light to the image pickup section 330. The image pickup lens unit 320 includes, as shown in FIG. 20, an object lens 321, a focusing lens 322, and the wavelength variable interference filter 5 provided between the lenses.

The image pickup section 330 includes a light receiving element. The image pickup section 330 picks up an image of image light guided by the image pickup lens unit 320.

Such a spectral camera 300 can pick up a spectral image of light having desired wavelength by transmitting light having image pickup target wavelength using the wavelength variable interference filter 5.

Further, the wavelength variable interference filter in the embodiment of the invention may be used as a band-pass filter. For example, the wavelength variable interference filter can also be used in an optical laser apparatus that splits, with the wavelength variable interference filter, only light in a narrow band having the center in predetermined wavelength among lights in a predetermined wavelength region emitted by the light emitting element and transmits the light.

The wavelength variable interference filter in the embodiment of the invention may also be used in a biometric identification apparatus. For example, the wavelength variable interference filter can be applied as well to an authenticating apparatus for authenticating a blood vessel, a fingerprint, a retina, or an iris using light in a near infrared region or a visible region.

Furthermore, the optical module and the electronic apparatus can be used as a density detecting apparatus. In this case, the density detecting apparatus splits, with the wavelength variable interference filter, infrared energy (infrared light) emitted from a substance, analyzes the infrared energy, and measures a subject density in a sample.

As explained above, the wavelength variable interference filter, the optical module, and the electronic apparatus in the embodiment of the invention can be applied to any apparatus that splits predetermined light from incident light. The wavelength variable interference filter in the embodiment of the invention can split plural wavelengths using one device. Therefore, it is possible to accurately carry out measurement of spectra having plural wavelengths and detection of plural components. Therefore, compared with an apparatus in that past that extracts desired wavelength using plural devices, it is possible to promote a reduction in the sizes of the optical module and the electronic apparatus. The optical module and the electronic apparatus can be suitably used as, for example, portable and vehicle-mounted optical devices.

Besides, specific structure in carrying out the invention can be changed as appropriate to other structures and the like within a range in which the object of the invention can be attained.

The entire disclosure of Japanese Patent Application No. 2011-215598 filed Sep. 29, 2011 is expressly incorporated by reference herein.

What is claimed is:

1. A wavelength variable interference filter comprising:
   a first substrate;
   a second substrate opposed to the first substrate;
   a first reflective film provided above the first substrate and configured to reflect a part of incident light and transmit a part of the incident light;
   a second reflective film provided above the second substrate, configured to reflect a part of incident light and transmit a part of the incident light, and opposed to the first reflective film via an inter-reflective film gap, which is a distance between surfaces of the second reflective film and the first reflective film;
   a first electrode provided above the first substrate;
   a second electrode provided above the second substrate and opposed to the first electrode via an inter-electrode gap, which is a distance between surfaces of the second electrode and the first electrode;
   a third electrode surrounding, in a plan view from a thickness direction of the first substrate and the second substrate, the first electrode excluding a part of a circumference of the first electrode and in non-contact with the first electrode and grounded; and
   a fourth electrode surrounding, in the plan view, the second electrode excluding a part of a circumference of the second electrode and in non-contact with the second electrode and grounded.

2. The wavelength variable interference filter according to claim 1, wherein
   the second substrate includes a movable section and a holding section that has a thickness dimension smaller than a thickness dimension of the movable section and holds the movable section to be capable of advancing and retracting with respect to the first substrate, and
   the second reflective film and the second electrode are provided on the movable section.

3. The wavelength variable interference filter according to claim 2, wherein the fourth electrode is provided on the movable section.

4. The wavelength variable interference filter according to claim 2, wherein the fourth electrode is provided over an entire surface of the holding section opposed to the first substrate.

5. The wavelength variable interference filter according to claim 4, wherein the fourth electrode includes a plurality of openings, from which the holding section is exposed, in plan view of the second substrate viewed from the substrate thickness direction, and the openings are equally arranged over the entire surface of the holdings section opposed to the first substrate.

6. The wavelength variable interference filter according to claim 1, wherein
the third electrode is connected to the first reflective film, and
the fourth electrode is connected to the second reflective film.

7. The wavelength variable interference filter according to claim 1, further comprising:
a first detection electrode connected to the first reflective film; and
a second detection electrode connected to the second reflective film, wherein
the third electrode is provided along an outer circumferential edge of the first detection electrode and in non-contact with the first detection electrode, and
the fourth electrode is provided along an outer circumferential edge of the second detection electrode and in non-contact with the second detection electrode.

8. The wavelength variable interference filter according to claim 1, wherein the dimension of the inter-reflective film gap is changed by applying a voltage between the first electrode and the second electrode.

9. An optical filter device comprising:
the wavelength variable interference filter according to claim 1; and
a housing configured to store the wavelength variable interference filter.

10. An optical module comprising:
the wavelength variable interference filter according to claim 1; and
a detecting section configured to detect light extracted by the first reflective film and the second reflective film.

11. An electronic apparatus comprising the wavelength variable interference filter according to claim 1.

12. A wavelength variable interference filter comprising:
a first substrate;
a second substrate opposed to the first substrate;
a first reflective film provided above the first substrate and configured to reflect a part of incident light and transmit a part of the incident light;
a second reflective film provided above the second substrate, configured to reflect a part of incident light and transmit a part of the incident light, and opposed to the first reflective film via an inter-reflective film gap, which is a distance between surfaces of the second reflective film and the first reflective film;
a first electrode provided above the first substrate;
a second electrode provided above the second substrate and opposed to the first electrode via an inter-electrode gap, which is a distance between surfaces of the second electrode and the first electrode;
a third electrode surrounding, in a plan view from a thickness direction of the first substrate and the second substrate, the first electrode excluding a part of a circumference of the first electrode and in non-contact with the first electrode and fixed to reference potential; and
a fourth electrode surrounding, in the plan view, the second electrode excluding a part of a circumference of the second electrode and in non-contact with the second electrode and fixed to the reference potential.

* * * * *